US007983751B2

(12) United States Patent
Zdeblick et al.

(10) Patent No.: US 7,983,751 B2
(45) Date of Patent: Jul. 19, 2011

(54) MEASURING CONDUCTION VELOCITY USING ONE OR MORE SATELLITE DEVICES

(75) Inventors: Mark J. Zdeblick, Portola Valley, CA (US); Timothy Robertson, Belmont, CA (US); George M. Savage, Portola Valley, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 397 days.

(21) Appl. No.: 12/063,097

(22) PCT Filed: Aug. 9, 2006

(86) PCT No.: PCT/US2006/031152
§ 371 (c)(1),
(2), (4) Date: Jun. 5, 2008

(87) PCT Pub. No.: WO2007/021804
PCT Pub. Date: Feb. 22, 2007

(65) Prior Publication Data
US 2008/0306394 A1 Dec. 11, 2008

Related U.S. Application Data

(60) Provisional application No. 60/707,913, filed on Aug. 12, 2005, provisional application No. 60/747,659, filed on May 18, 2006.

(51) Int. Cl.
*A61N 1/00* (2006.01)
(52) U.S. Cl. ............................................... 607/9
(58) Field of Classification Search .................. 600/373, 600/508, 509; 607/9, 2, 27, 19, 17, 122, 607/119, 332, 61
See application file for complete search history.

(56) References Cited

U.S. PATENT DOCUMENTS

| 2,956,586 A | 10/1960 | Zeigler et al. |
| 3,888,260 A | 6/1975 | Fischell |
| 3,985,123 A | 10/1976 | Herzlinger et al. |
| 4,164,946 A | 8/1979 | Langer |
| 4,262,982 A | 4/1981 | Kenny |

(Continued)

FOREIGN PATENT DOCUMENTS

EP 0659388 6/1995

(Continued)

OTHER PUBLICATIONS

Auricchio et al., "The Pacing Therapies for Congestive Heart Failure (PATH-CHF) Study: Rationale, Design and Endpoints of a Prospective Randomized Multicenter Study" Am J. Cardio.: 83:130D-135D (1999).

(Continued)

*Primary Examiner* — George Manuel
*Assistant Examiner* — Robert N Wieland
(74) *Attorney, Agent, or Firm* — Bret E. Field; Bozicevic Field & Francis LLP.

(57) ABSTRACT

A method for measuring the conduction velocity of a depolarization wave in a tissue employs a first satellite located within the tissue and a second that satellite is located within the tissue a distance away from the first satellite, e.g., by using the time of depolarization wave as reported from each satellite and the distance to determine velocity of the wave. Also provided are systems and kits that find use in accordance with the invention.

43 Claims, 19 Drawing Sheets

U.S. PATENT DOCUMENTS

| | | | |
|---|---|---|---|
| 4,397,314 A | 8/1983 | Vaguine | |
| 4,399,820 A | 8/1983 | Wirtzfeld et al. | |
| 4,600,454 A | 7/1986 | Plummer | |
| 4,603,705 A | 8/1986 | Speicher et al. | |
| 4,628,934 A | 12/1986 | Pohndorf et al. | |
| 4,628,935 A | 12/1986 | Jones et al. | |
| 4,750,494 A * | 6/1988 | King | 607/14 |
| 4,776,334 A | 10/1988 | Prionas | |
| 4,815,472 A | 3/1989 | Wise et al. | |
| 4,877,032 A | 10/1989 | Heinze et al. | |
| 4,878,898 A | 11/1989 | Griffin et al. | |
| 4,881,410 A | 11/1989 | Wise et al. | |
| 4,902,273 A | 2/1990 | Choy et al. | |
| 5,004,275 A | 4/1991 | Miller | |
| 5,005,613 A | 4/1991 | Stanley | |
| 5,035,246 A | 7/1991 | Heuvelmans et al. | |
| 5,072,737 A | 12/1991 | Goulding | |
| 5,113,868 A | 5/1992 | Wise et al. | |
| 5,156,154 A | 10/1992 | Valenta, Jr. et al. | |
| 5,158,536 A | 10/1992 | Sekins et al. | |
| 5,176,619 A | 1/1993 | Segalowitz | |
| 5,188,106 A | 2/1993 | Nappholz et al. | |
| 5,209,238 A | 5/1993 | Sundhar | |
| 5,213,098 A | 5/1993 | Bennett et al. | |
| 5,243,981 A * | 9/1993 | Hudrlik | 607/11 |
| 5,285,744 A | 2/1994 | Grantham et al. | |
| 5,304,208 A | 4/1994 | Inuaggiato et al. | |
| 5,305,745 A | 4/1994 | Zacouto et al. | |
| 5,313,020 A | 5/1994 | Sackett | |
| 5,391,199 A | 2/1995 | Ben-Haim | |
| 5,411,532 A | 5/1995 | Mortazavi | |
| 5,411,537 A | 5/1995 | Munshi et al. | |
| 5,417,717 A | 5/1995 | Salo et al. | |
| 5,419,767 A | 5/1995 | Eggers et al. | |
| 5,423,323 A | 6/1995 | Orth | |
| 5,433,198 A | 7/1995 | Desai | |
| 5,509,411 A | 4/1996 | Littmann et al. | |
| 5,535,752 A | 7/1996 | Halperin et al. | |
| 5,544,656 A | 8/1996 | Pitsillides et al. | |
| 5,549,650 A | 8/1996 | Bornzin et al. | |
| 5,579,234 A | 11/1996 | Wiley et al. | |
| 5,579,764 A | 12/1996 | Goldreyer | |
| 5,591,142 A | 1/1997 | Van Erp | |
| 5,593,430 A | 1/1997 | Renger | |
| 5,628,777 A | 5/1997 | Moberg et al. | |
| 5,662,587 A | 9/1997 | Grundfest et al. | |
| 5,674,258 A | 10/1997 | Henschel et al. | |
| 5,676,153 A | 10/1997 | Smith et al. | |
| 5,683,429 A | 11/1997 | Mehra | |
| 5,713,937 A | 2/1998 | Nappholz et al. | |
| 5,720,768 A | 2/1998 | Verboven-Nelissen | |
| 5,743,267 A | 4/1998 | Nikolic et al. | |
| 5,751,050 A | 5/1998 | Ishikawa et al. | |
| 5,788,647 A | 8/1998 | Eggers | |
| 5,797,903 A | 8/1998 | Swanson et al. | |
| 5,800,460 A | 9/1998 | Powers et al. | |
| 5,800,465 A | 9/1998 | Thompson et al. | |
| 5,810,735 A | 9/1998 | Halperin et al. | |
| 5,814,089 A | 9/1998 | Stokes et al. | |
| 5,836,987 A | 11/1998 | Baumann et al. | |
| 5,873,849 A | 2/1999 | Bernard | |
| 5,902,234 A | 5/1999 | Webb | |
| 5,902,248 A | 5/1999 | Millar et al. | |
| 5,913,814 A | 6/1999 | Zantos | |
| 5,924,997 A | 7/1999 | Campbell | |
| 5,935,084 A | 8/1999 | Southworth | |
| 5,938,690 A | 8/1999 | Law et al. | |
| 5,941,904 A | 8/1999 | Johnston et al. | |
| 5,957,957 A | 9/1999 | Sheldon | |
| 5,991,661 A | 11/1999 | Park et al. | |
| 5,999,848 A | 12/1999 | Gord et al. | |
| 5,999,849 A | 12/1999 | Gord et al. | |
| 6,002,963 A | 12/1999 | Mouchawar et al. | |
| 6,009,349 A | 12/1999 | Mouchawar et al. | |
| 6,015,386 A | 1/2000 | Kensey et al. | |
| 6,024,704 A | 2/2000 | Meador et al. | |
| 6,032,699 A | 3/2000 | Cochran et al. | |
| 6,033,398 A | 3/2000 | Farley et al. | |
| 6,038,480 A | 3/2000 | Hrdlicka et al. | |
| 6,044,297 A | 3/2000 | Sheldon et al. | |
| 6,044,299 A | 3/2000 | Nilsson | |
| 6,058,329 A | 5/2000 | Salo et al. | |
| 6,061,593 A | 5/2000 | Fischell et al. | |
| 6,077,136 A | 6/2000 | Arai et al. | |
| 6,078,830 A | 6/2000 | Levin et al. | |
| 6,081,748 A | 6/2000 | Struble et al. | |
| 6,115,626 A | 9/2000 | Whayne et al. | |
| 6,115,636 A | 9/2000 | Ryan | |
| 6,120,442 A | 9/2000 | Hickey | |
| 6,141,588 A * | 10/2000 | Cox et al. | 607/9 |
| 6,155,267 A | 12/2000 | Nelson | |
| 6,163,716 A | 12/2000 | Edwards et al. | |
| 6,163,725 A | 12/2000 | Peckham et al. | |
| 6,165,135 A | 12/2000 | Neff | |
| 6,171,252 B1 | 1/2001 | Roberts | |
| 6,197,021 B1 | 3/2001 | Panescu et al. | |
| 6,197,677 B1 | 3/2001 | Lee et al. | |
| 6,206,835 B1 | 3/2001 | Spillman, Jr. et al. | |
| 6,206,874 B1 | 3/2001 | Ubby et al. | |
| 6,223,080 B1 | 4/2001 | Thompson | |
| 6,234,973 B1 | 5/2001 | Meador et al. | |
| 6,264,606 B1 | 7/2001 | Ekwall et al. | |
| 6,277,078 B1 | 8/2001 | Porat et al. | |
| 6,287,256 B1 | 9/2001 | Park et al. | |
| 6,299,582 B1 | 10/2001 | Brockway et al. | |
| 6,301,500 B1 | 10/2001 | Van Herk et al. | |
| 6,309,350 B1 | 10/2001 | VanTassel et al. | |
| 6,309,385 B1 | 10/2001 | Simpson | |
| 6,328,699 B1 | 12/2001 | Eigler et al. | |
| 6,360,123 B1 | 3/2002 | Kimchi et al. | |
| 6,363,279 B1 | 3/2002 | Ben-Haim et al. | |
| 6,366,811 B1 | 4/2002 | Carlson | |
| 6,370,431 B1 | 4/2002 | Stoop et al. | |
| 6,406,677 B1 | 6/2002 | Carter et al. | |
| 6,418,348 B1 | 7/2002 | Witte | |
| 6,421,567 B1 | 7/2002 | Witte | |
| 6,438,408 B1 | 8/2002 | Mulligan et al. | |
| 6,466,820 B1 | 10/2002 | Juran et al. | |
| 6,473,638 B2 | 10/2002 | Ferek-Petric | |
| 6,473,653 B1 | 10/2002 | Schallhorn et al. | |
| 6,477,395 B2 | 11/2002 | Schulman et al. | |
| 6,477,417 B1 | 11/2002 | Levine | |
| 6,484,727 B1 | 11/2002 | Vaska et al. | |
| 6,496,730 B1 | 12/2002 | Kleckner et al. | |
| 6,580,946 B2 | 6/2003 | Struble | |
| 6,584,362 B1 | 6/2003 | Scheiner et al. | |
| 6,600,954 B2 | 7/2003 | Cohen et al. | |
| 6,611,714 B1 | 8/2003 | Mo | |
| 6,625,493 B2 | 9/2003 | Kroll et al. | |
| 6,628,989 B1 | 9/2003 | Penner et al. | |
| 6,666,826 B2 | 12/2003 | Salo et al. | |
| 6,812,796 B2 | 11/2004 | Pryanishnikov et al. | |
| 6,885,889 B2 | 4/2005 | Chinchoy | |
| 6,934,584 B1 | 8/2005 | Wong et al. | |
| 6,978,184 B1 | 12/2005 | Marcus et al. | |
| 6,993,384 B2 | 1/2006 | Bradley et al. | |
| 6,994,676 B2 | 2/2006 | Mulligan et al. | |
| 7,047,084 B2 | 5/2006 | Erickson et al. | |
| 7,174,218 B1 | 2/2007 | Kuzma | |
| 7,200,439 B2 | 4/2007 | Zdeblick et al. | |
| 7,204,798 B2 | 4/2007 | Zdeblick et al. | |
| 7,214,189 B2 | 5/2007 | Zdeblick et al. | |
| 7,236,821 B2 * | 6/2007 | Cates et al. | 607/2 |
| 7,267,649 B2 | 9/2007 | Zdeblick et al. | |
| 7,467,016 B2 | 12/2008 | Colborn | |
| 2001/0000187 A1 | 4/2001 | Peckham et al. | |
| 2001/0002924 A1 | 6/2001 | Tajima | |
| 2001/0025192 A1 | 9/2001 | Gerber et al. | |
| 2001/0047138 A1 | 11/2001 | Kokate et al. | |
| 2001/0053882 A1 | 12/2001 | Haddock et al. | |
| 2002/0026183 A1 | 2/2002 | Simpson | |
| 2002/0040236 A1 | 4/2002 | Lau et al. | |
| 2002/0045921 A1 | 4/2002 | Wolinsky et al. | |
| 2002/0077568 A1 | 6/2002 | Haddock | |
| 2002/0077673 A1 | 6/2002 | Penner et al. | |
| 2002/0095196 A1 | 7/2002 | Linberg | |
| 2002/0099419 A1 | 7/2002 | Cohen et al. | |

| | | | | | | |
|---|---|---|---|---|---|---|
| 2002/0111560 A1 | 8/2002 | Kokate et al. | | EP | 1136033 | 9/2001 |
| 2002/0120186 A1 | 8/2002 | Keimel | | EP | 1266606 | 12/2002 |
| 2002/0151816 A1 | 10/2002 | Rich et al. | | EP | 1426079 | 6/2004 |
| 2002/0156417 A1 | 10/2002 | Rich et al. | | EP | 1938861 | 7/2008 |
| 2002/0161307 A1 | 10/2002 | Yu et al. | | FR | 2097337 | 2/1972 |
| 2002/0169445 A1 | 11/2002 | Jain et al. | | JP | 6456031 | 2/1988 |
| 2002/0193859 A1 | 12/2002 | Schulman et al. | | JP | 2-99036 | 4/1990 |
| 2003/0078623 A1 | 4/2003 | Weinberg et al. | | JP | 3-055032 | 3/1991 |
| 2003/0105496 A1 | 6/2003 | Yu et al. | | JP | 5269136 | 10/1993 |
| 2003/0153952 A1 | 8/2003 | Auricchio et al. | | JP | 6501177 | 2/1994 |
| 2003/0191502 A1 | 10/2003 | Sharma et al. | | JP | 6-506619 | 4/1994 |
| 2004/0024440 A1 | 2/2004 | Cole | | JP | 7-542 | 1/1995 |
| 2004/0039417 A1 | 2/2004 | Soykan et al. | | JP | 2000139833 | 5/2000 |
| 2004/0093053 A1 | 5/2004 | Gerber et al. | | JP | 2000350705 | 12/2000 |
| 2004/0097965 A1 | 5/2004 | Gardeski et al. | | JP | 2002272758 | 9/2002 |
| 2004/0098074 A1 | 5/2004 | Erickson et al. | | WO | WO9952588 | 10/1999 |
| 2004/0143154 A1 | 7/2004 | Lau et al. | | WO | WO0143821 | 6/2001 |
| 2004/0193021 A1 | 9/2004 | Zdeblick et al. | | WO | WO0195787 | 12/2001 |
| 2004/0199235 A1 | 10/2004 | Younis | | WO | WO02063228 | 7/2002 |
| 2004/0215049 A1 | 10/2004 | Zdeblick et al. | | WO | WO02065894 | 8/2002 |
| 2004/0220637 A1 | 11/2004 | Zdeblick et al. | | WO | WO2004020040 | 3/2004 |
| 2004/0254483 A1 | 12/2004 | Zdeblick et al. | | WO | WO2004052182 | 6/2004 |
| 2004/0260346 A1 | 12/2004 | Overall et al. | | WO | WO2004066814 | 8/2004 |
| 2005/0027320 A1 | 2/2005 | Nehls et al. | | WO | WO2004066817 | 8/2004 |
| 2005/0054892 A1 | 3/2005 | Lau et al. | | WO | WO2004066825 | 8/2004 |
| 2005/0090870 A1* | 4/2005 | Hine et al. ............. 607/17 | | WO | WO2004067081 | 8/2004 |
| 2005/0102011 A1 | 5/2005 | Lau et al. | | WO | 2006/029090 | 3/2006 |
| 2005/0149138 A1* | 7/2005 | Min et al. ............. 607/27 | | WO | 2006/042039 A2 | 4/2006 |
| 2005/0246004 A1 | 11/2005 | Cameron et al. | | WO | 2006/069322 | 6/2006 |
| 2005/0267542 A1 | 12/2005 | David et al. | | WO | WO2006069323 | 6/2006 |
| 2006/0058588 A1 | 3/2006 | Zdeblick | | WO | WO2006073915 | 7/2006 |
| 2006/0122678 A1 | 6/2006 | Olsen et al. | | WO | 2006/105474 | 10/2006 |
| 2006/0161211 A1 | 7/2006 | Thompson et al. | | WO | 2007/005641 | 1/2007 |
| 2006/0247539 A1 | 11/2006 | Schugt et al. | | WO | WO2007075974 | 7/2007 |
| 2006/0265038 A1 | 11/2006 | Hagen et al. | | WO | WO2007120884 | 10/2007 |
| 2007/0100399 A1 | 5/2007 | Parramon et al. | | WO | WO2007149546 | 12/2007 |
| 2007/0179569 A1 | 8/2007 | Zdeblick | | WO | WO2008004010 | 1/2008 |
| 2007/0198066 A1 | 8/2007 | Greenberg et al. | | WO | WO2008008755 | 1/2008 |
| 2007/0203517 A1 | 8/2007 | Williams et al. | | WO | WO2008027639 | 3/2008 |
| 2007/0219591 A1 | 9/2007 | Zdeblick et al. | | | | |
| 2007/0219608 A1 | 9/2007 | Swoyer et al. | | | | |

OTHER PUBLICATIONS

Borky at al., "Integrated Signal Conditioning for Silicon Pressure Sensors" IEEE Transactions on Electron Devices ED-26(12): 1906-1910 (1979).

Kovacs et al., "Technology Development for a Chronic Neutral Interface" A dissertation, Stanford University Aug. 1990 pp. 9, 225-234, 257, 276.

Little at al, "The Output of the Heart and its Control" Physiology of the Heart and Circulation, 4th ed. 1989 Year Book Medical Publishers Inc. pp. 165-187.

Paolocci et al., "Positive inotropic and lusitropic effects of HNO/NO in failing hearts: Independence from β-adrenergic signaling" PNAS vol. 100, No. 9 (2003) 5537-5542.

Receveur et al., "Lateraly Moving Bi-Stable MEMS DC-Switch for Biomedical Applications" Medtronic Bakken Research Center, The Netherlands (2004) pp. 854-856.

U.S. Appl. No. 11/917,992, filed Jul. 13, 2009 (Specification, Claims, Abstract and Figures as filed); Jensen et al., (2009) "Deployable Epicardial Electrode and Sensor Array" 69pp.

U.S. Appl. No. 12/097,959, filed Nov. 17, 2008 (Specification, Claims, Abstract and Figures as filed); Zdeblick et al., (2008) "Implantable Integrated Circuit" 199pp.

U.S. Appl. No. 12/395,538, filed Feb. 27, 2009 (Specification, Claims, Abstract and Figures as filed); Bi et al., (2009) "Integrated Circuit Implementation and Fault Control System, Device, and Method" 163pp.

2007/0255336 A1 11/2007 Herbert et al.
2007/0255373 A1 11/2007 Metzler et al.
2008/0007186 A1 1/2008 Lu et al.
2008/0021292 A1 1/2008 Stypulkowski
2008/0027289 A1 1/2008 Zdeblick
2008/0039916 A1 2/2008 Colliou et al.
2008/0045826 A1 2/2008 Greenberg et al.
2008/0058656 A1 3/2008 Costello et al.
2008/0061630 A1 3/2008 Andreu et al.
2008/0091246 A1 4/2008 Carey et al.
2008/0097227 A1 4/2008 Zdeblick et al.
2008/0097566 A1 4/2008 Colliou
2008/0114230 A1 5/2008 Addis
2008/0140141 A1 6/2008 Ben-David et al.
2008/0140167 A1 6/2008 Hagen et al.
2008/0147168 A1 6/2008 Ransbury et al.
2008/0167702 A1 7/2008 Ransbury et al.
2008/0177343 A1 7/2008 Dal Molin et al.
2008/0255647 A1 10/2008 Jensen et al.
2008/0294062 A1 11/2008 Rapoport et al.
2008/0294218 A1 11/2008 Savage et al.
2008/0306394 A1 12/2008 Zdeblick et al.
2009/0024184 A1 1/2009 Sun et al.
2009/0054946 A1 2/2009 Sommer et al.
2009/0054947 A1 2/2009 Bourn et al.

FOREIGN PATENT DOCUMENTS

EP  1048321  11/2000
EP  1050265  11/2000

* cited by examiner

MEASURING CONDUCTION VELOCITY USING ONE OR MORE SATELLITE DEVICES

CROSS-REFERENCE TO RELATED APPLICATIONS

Pursuant to 35 U.S.C. §119 (e), this application claims priority to the filing date of: U.S. Provisional Patent Application Ser. No. 60/707,913 filed Aug. 12, 2005; and U.S. Provisional Patent Application Ser. No. 60/747,659 filed May 18, 2006; the disclosures of which are herein incorporated by reference.

INTRODUCTION

1. Field of the Invention

The present invention relates to administering and monitoring electrical signals in living tissue and more particularly to the measurement of the conduction velocity of a depolarization wave in living tissue using one or more satellite devices.

2. Background of the Invention

Many people die of congestive heart failure every year. Congestive heart failure is a condition that reduces the flow of blood and is typically characterized by breathlessness, weakness, edema in the lungs and the lower portions of the body, and abdominal discomfort. These symptoms are associated with the inability of the heart to pump sufficient blood, which may be associated with either the left ventricle, the right ventricle, or both. A possible cause of cardiac output insufficiency may be the failure of the heart to contract efficiently.

The heart is a mechanical pump that is stimulated by electrical impulses and causes blood to flow throughout the body. During a normal heart beat, blood flows throughout the body in a sequence of steps. First, the right atrium (RA) is filled with blood from the returning veins. Second, the RA contracts causing the blood from the RA to move into the right ventricle (RV). Third, the RV contracts causing the blood from the RV to move into and through the lungs. Fourth, after the blood is pumped through the lungs it moves back to the heart but into the left atrium (LA). Fifth, the LA contracts causing blood from the LA to move into the left ventricle (LV). Sixth the blood is then pumped throughout the entire body. A series of four heart valves are used to keep the blood flowing in one direction.

The electrical impulses that stimulate the heart causing these mechanical contractions, or heart beats, originate in the sino-atrial node. These electrical impulses are called normal sinus rhythm and occur approximately 72 times per minute in normal individuals. The sino-atrial node contains a group of specialized heart cells (cardiac cells) in the RA that automatically change their voltage potential (i.e. depolarize). When these cardiac cells depolarize a depolarization wave is generated. The depolarization wave propagates across the cells of both atria causing atrial contraction. When the advancing depolarization wave front reaches the A-V node it is delayed so that the contracting atria have time to fill the ventricles with blood. After the delay, the depolarizing wave front passes over the ventricles, causing the ventricles to contract and pump blood to the lungs and throughout the body.

Depolarization occurs when the electrically polarized cardiac cells change their voltage potential. This change in voltage potential causes a cascade effect in which adjacent cells sequentially change their voltage potential generating a depolarization wave which spreads and travels from cell to cell across the entire heart. This depolarization wave is typically detected by electrodes placed on the surface of the body. After all the cells are depolarized, the cardiac cells are repolarized and restored to their resting potential. One method of detecting a depolarization wave is with an electrocardiogram (ECG). An ECG is a graphical recording of the changes occurring in the voltage potential between different sites on the skin as a result of heart activity.

The conduction velocity is a measure of how fast the depolarization wave travels in the cardiac tissue. A variety of different types of informative data can be obtained from the determination of conduction velocity. Therefore, there is continued interest in the development of methods and systems that can be employed to determine conduction velocity in cardiac tissue. Of particular interest would be the development of such system that could readily identify not only velocity but also direction of wave movement.

SUMMARY

Embodiments of the present invention provide techniques and systems for measuring conduction velocity in tissue, such as in the heart. The subject systems and methods provide for ready determination of conduction velocity using implantable systems that may also be employed for therapy, where the therapy may be electrical stimulation therapy which is delivered by the same system and is determined based on the conduction velocity data obtained by the system. Embodiments of the systems and methods provide for ready determination of the direction of wave depolarization through a tissue of interest, and can be employed to determine areas of abnormal wave conduction, e.g., pre-ischemic or ischemic areas of tissue. The subject invention allows for the evaluation of wave conduction through a tissue in response to an applied stimulus of interest, such as a electrical stimulation, pharmacological stimulation, exercise, etc. The data obtained by the system can be readily evaluated and employed to determine precise therapeutic approaches, e.g., electrical stimulation or pacing therapy, which approaches are uniquely tailored to the needs of a particular patient.

In embodiments of the present invention, one or more individually addressable modular circuits ("satellites" or "satellite units") are placed in the tissue of interest at various locations, such that there is at least a first satellite and a second satellite that is placed in the tissue a distance from the first satellite. In certain embodiments, the satellites are part of a multiplex system, e.g., where they are placed along a bus that includes at least one conductor associated with a carrier, such as a pacing lead. The satellite-bearing carrier is intended to be implanted or otherwise inserted into tissue (e.g., the heart) so as to interact with the tissue. The one or more satellites, depending on the embodiment, may be coupled via the bus to a device such as a pacemaker that provides power and includes control circuitry. For convenience, this device will be referred to as the central controller, although it may itself be a distributed system.

In certain embodiments, the methods and systems determine conduction velocity in a tissue in response to an applied stimulus to the tissue. The stimulus may vary, from electrical to pharmacological to environmental (e.g., exercise). In certain embodiments, one of the satellites can be used to stimulate the tissue with a depolarization signal, in which case the time of the stimulation can be considered the time of the detection for that satellite.

In certain embodiments, the methods include the use of two or more sets of two or more satellites to determine the direction of wave travel through the tissue. The direction can be determined in two dimensions or three dimensions through appropriate provision of sets of satellites. Such methods may include evaluating a region of tissue for abnormal wave conduction, which may be in response to an applied stimulus as described above.

In certain embodiments, following evaluation of conduction velocity, the methods may include applying therapy to a patient based on the conduction velocity evaluation. For example, electrical therapy, such as pacing therapy, may be applied to cardiac tissue based on the determined depolarization wave velocity data, e.g., one dimensional, two-dimensional or three-dimensional, obtained for that tissue.

Also provided by the invention is a particular type of therapy referred to herein as cardiac wavefront controller therapy, where this particular therapy may be (though is not necessarily) coupled with the depolarization wave velocity evaluation methods as reviewed above.

In these embodiments, the cardiac wavefront controller provides an interactive, low voltage treatment for atrial fibrillation, atrial flutter and arrhythmias, which may be associated with regions of abnormal depolarization wave conduction. The treatment may be provided by multiple electrode leads or array patches, e.g., as developed by some of the present inventors and described in greater detail below.

In certain embodiments of the invention, the multielectrode lead or array patch is positioned in the heart or near the heart. The multiple electrodes on these devices (which may be the same device as employed to evaluate depolarization wave velocity) are activated in a specific manner to break the spasmodic effect of electrical pulses in the heart, e.g., in the region of abnormal conduction, that leads to fibrillation and flutter. The strategy for the activation, including timing, energy level, electrode satellite and segment selection, and activation order can be facilitated by information obtained by local sensors on the lead. In some cases these sensors are the electrodes functioning in a dual capacity. Preset software "scripts" of these strategies can be employed to optimize results and minimize instillation time and cost.

DETAILED DESCRIPTION

Figure 1:
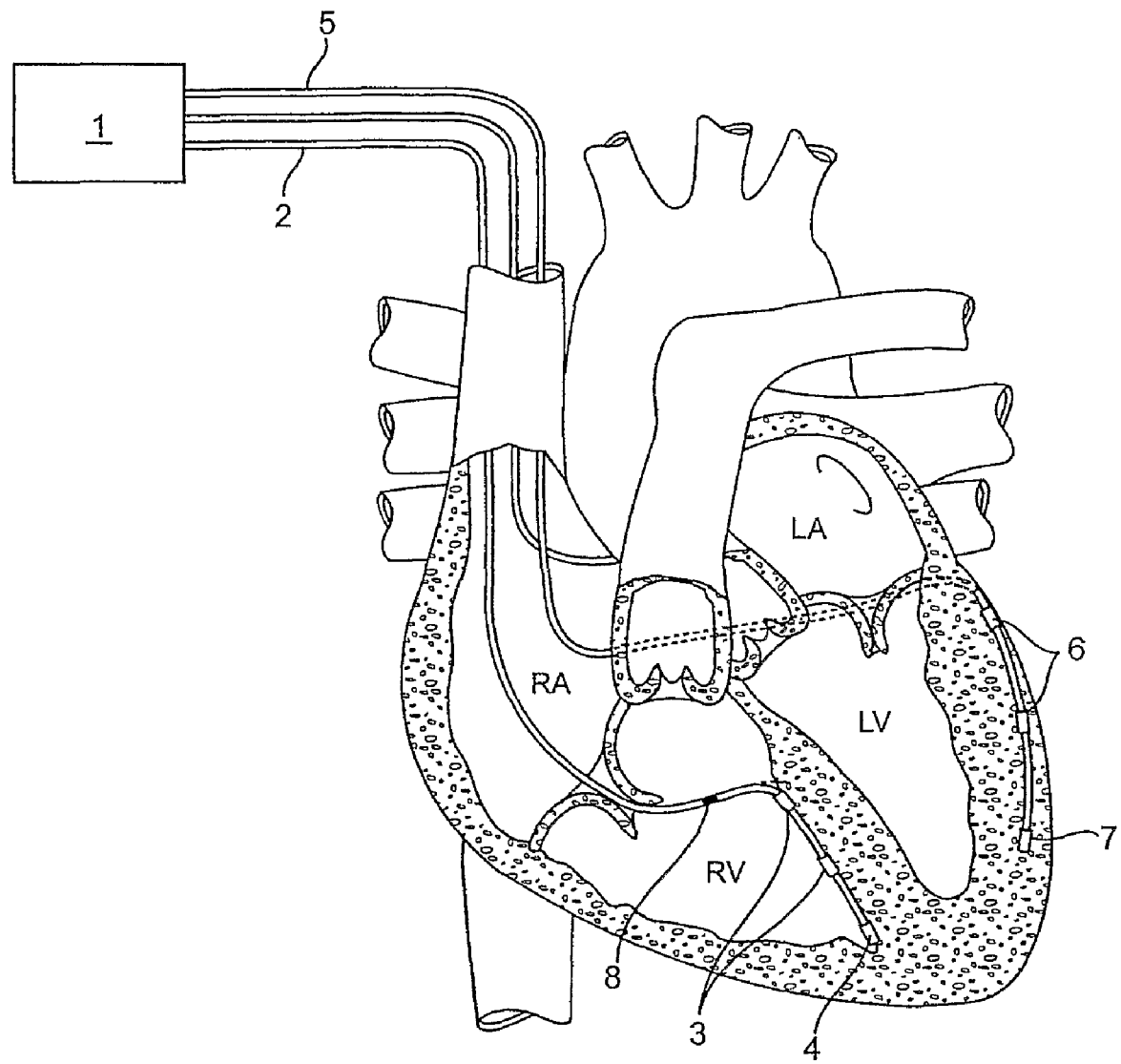
FIG. 1 illustrates the location of a number of satellites in a human heart, in accordance with an embodiment of the present invention.

The precise measurement of signal conduction velocity, such as depolarization wave velocity, can be very useful in assisting forms of treatments. Determination of depolarization wave velocity through cardiac tissue in one-, two- and even three-dimensions, as provided by the present invention, provides for extremely useful data in both the detection of regions of abnormal wave conduction which can lead to pathological conditions, as well in the determination of appropriate therapies for a patient. For example, the ideal dosage of certain medication can be assessed by monitoring different tissue conduction velocities. The present invention provides systems and devices for readily determining depolarization wave velocity through a tissue in one-, two- and even three-dimensions.

In further describing various embodiments and aspects of the invention, an overview of the methods and systems in accordance with the invention is first provided. Next, illustrative embodiments of various systems and methods for determining conduction velocity through cardiac tissue are provided. Following this, a review of cardiac wavefront controllers and methods of use is provided. Finally, additional aspects of the invention, such as illustrative applications in which the invention finds use, as well as computer related embodiments and kits, are described in greater detail.

Overview

The present invention provides a system and method for measuring the conduction velocity in tissue, where the measurement may be in one-, two or even three-dimensions. Embodiments of the invention employ a signal detection system having a number of elements (satellites), e.g., where "number" means at least a first and a second satellite. Each satellite may be controlled by an integrated circuit (control chip), such as an integrated low-power circuit, that is part of the satellite itself. The satellites may also include one or more distinct effectors, e.g., sensors and actuators (in the form of electrodes), etc., which are coupled to the integrated circuit (IC). The satellites are in communication with a central control unit, where communication may conveniently be provided by a multiplex format, where the format may be characterized by the presence of two wires, one wire or even zero wires (see e.g., the format described in U.S. Patent Application Ser. No. 60/713,680; the disclosure of which zero-wire format is specifically disclosed herein by reference). In certain embodiments, the satellites are each coupled to central controller through two wires or one wire. Further details of such "multiplex" systems are described below, but can also be found in copending U.S. application Ser. Nos. 10/734,490 and 11/249,152, as well as PCT application serial No. PCT/US2005/031559 and PCT/US2005/039535; the disclosures of which multiplex systems are herein incorporated by reference.

Each satellite includes satellite circuitry and one or more devices, e.g., effectors, that interact with the tissue. The satellite circuitry includes at (east one active device, and may be an integrated circuit ("satellite chip"). The satellite circuitry is coupled to the bus, and thus interfaces the central controller to the one or more devices. The devices that interact with the body ("interacting devices") may function as activators, sensors, or both. For example, these interacting devices may be electrodes that are used to introduce analog electrical signals (e.g., one or more pacing pulses) into the living tissue in the local areas where the electrodes are positioned (e.g., heart muscles) or to sense analog signals (e.g., a propagating depolarization signal) within the living tissue.

The bus may carry analog and digital signals, and, at various times during operation, may be used to do one or more of the following: transmit address information from the central controller to the satellites, send configuration information from the central controller to the satellites to configure one or multiple electrodes associated with selected satellites, provide a power supply to operate the digital logic circuits within the satellite chip, transmit activation pulses from the central controller to the satellites, and transmit analog signals from the satellites to the central controller.

Conduction velocity may be measured by using one or more satellites to detect the polarization signal as it propagates past the one or more satellites, using the bus to communicate with the central controller, and computing the velocity based on a time difference between the polarization signal being detected at two spaced satellites. The term "detecting the polarization signal" is used broadly.

In some embodiments, the satellite is configured to couple a pair of its electrodes, which are in contact with the tissue, to the bus so the central controller can sense the analog voltage that appears across the electrodes. The central controller performs the operations required to determine when the analog signal from the satellite represents the depolarization signal, for example by determining that the voltage has exceeded a threshold (or met some other set of conditions) during the interval that the satellite has its electrodes coupled to the bus.

In other embodiments, the satellite includes additional circuitry so that the satellite, in addition to experiencing the voltages, can determine when the analog voltage across its electrodes meets a particular set of conditions, and can report such a determination to the central controller. This could, for example, be accomplished by the central controller polling the satellites (e.g., by sequentially configuring the satellites to send a digital signal on the bus), or by the satellite asserting an interrupt signal. For these embodiments the satellite may include additional functionality, for example, the ability to transmit digital signals. The satellite can be considered to have detected the depolarization signal, although the central controller may perform portions of the detection.

As indicated above and illustrated in the figures, the first and second satellites may be present on the carrier, such as the same lead. The lead may further contain one or more conductive elements, e.g., wires, to which the first and second satellites are coupled, e.g., to obtain power from a central controller and/or transmit data to a central controller.

In certain embodiments, the methods include detecting the conduction velocity of a wave through tissue in two dimensions or even three dimensions. In these embodiments where velocity measurements are obtained in two or three dimensions, directionality of conduction of the wave through the tissue of interest can also be determined, e.g., in two-dimensions or three-dimensions. In certain of these embodiments, two or more sets of satellites are employed to determine conduction velocity of a wave through tissue. In these embodiments the two or more sets (each containing two or more satellites) may be associated with the tissue in a non-linear arrangement so as to provide the desired velocity measurements in two or even three directions. In such embodiments, a measurement of conduction velocity may be obtained for each different set. Obtaining a conduction velocity measurement for each different set enables one to determine the direction of wave travel through the tissue. As such, the methods of certain embodiments include obtaining at least first and second velocity measurements from different sets of satellites, and then using these different measurements to determine the direction of wave travel through the tissue.

As such, embodiments of the methods may include obtaining first measure of conduction velocity from a set of first and second satellites and a second measure of conduction velocity from a set of third and fourth satellites, where the third and fourth satellites are positioned at a different location of the tissue, and then determining a direction of the depolarization wave in the tissue from said first and second measures of conduction velocity. Where two sets are employed, two-dimensional directional information of wave conduction may be determined. Similarly, where three sets of satellites are employed, three-dimensional direction information of wave conduction may be determined.

The different sets of satellites are non-linearly associated with the tissue. By non-linearly associated with the tissue is meant that the two or more sets of satellites define at least a two-dimensional plane, if not three-dimensional space (e.g., where three or more sets of satellites are present). As such, they can be used to obtain a measure of the wave velocity through the tissue at two or more different locations, and these different velocity measurements can then be employed to obtain more detailed information about the direction of wave propagation through the tissue. The number of different sets that may be employed in these embodiments may vary, such as two or more, three or more, four or more etc., where as the number of the different sets increases, the amount of detail with respect to wave propagation through the tissue is enhanced.

As described above, the satellites may be present on a carrier, e.g., a lead. The different sets of satellites employed in such embodiments may be present on the same or different leads, as desired. As such, in certain embodiments each set of satellites is present on a different lead. For example, a system may employ a set of first and second satellites present on a first lead and a set of third and fourth satellites present on a second lead.

While the different sets of satellites may be present on different leads, two or more sets may also be present on the same lead, e.g., where the lead is deployable such that it can provide for two or more sets of non-linear satellites. Deployable multiplexed leads and systems are reviewed in PCT application serial no. PCT/US2006/025648, the disclosure of which leads and systems is herein incorporated by reference.

Where desired, the depolarization wave conductive properties of a region of tissue may be evaluated. As such, the overall conductive properties of a two- or three-dimensional portion of tissue, such as cardiac tissue may be assessed. In this manner, regions of abnormal conductance, e.g., as compared to other regions of the tissue, may be identified. The regions of abnormal conductance may be caused by different underlying mechanisms, such as the presence of ischemic or pre-ischemic tissue, the presence of scar tissue, the presence of regions of non-linear, e.g., curvilinear, wave conduction (such as reentrant circuits described below), etc. As such, methods of the invention include evaluating the obtained data concerning wave conduction velocity and/or direction to identify regions of abnormal wave conduction through the tissue of interest, e.g., ischemic regions, pre-ischemic regions, regions of non-linear conduction, etc., which regions can give rise to a variety of different disease conditions, as reviewed in greater detail below.

In certain embodiments, a stimulus is applied to the tissue and the conductive properties of the tissue (e.g., as described above) are evaluated in response to the applied stimulus. The applied stimulus may vary, from pharmaceutical to electrical to physical/environmental. As such, the stimulus may be a pharmaceutical stimulus, e.g., that is provided by a patient being administered a medication, such that conduction velocity is evaluated in response to the administered medication. The stimulus may also be an electrical stimulus, e.g., that is applied to the tissue from one of the satellites, as reviewed below. The stimulus may also be a physical or environmental stimulus that is applied to the host that comprises the tissue of interest, where the stimulus may be a change in temperature, the performance of strenuous activity, e.g., exercise, etc. For example, the conduction velocity of cardiac tissue could be evaluated while a patient is exercising, e.g., to detect the presence of pre-ischemic regions of cardiac tissue that exhibit abnormal conductive properties when a patient is exercising. Such regions may not appear when a patient is not exercising. As such, the present invention provides an important new tool for identifying and assessing such regions.

In certain embodiments, following detection/evaluation of a region of abnormal wave conduction, the method further includes administering a therapy to the patient, where the administered therapy is based, at least in part, on the obtained conduction velocity data from the patient. As such, the methods may include applying a stimulus to the tissue of interest in a manner sufficient to compensate for an identified region of abnormal depolarization wave conduction. In certain of these embodiments, the methods may include use of a cardiac wavefront controller (described in greater detail below) to apply the compensating stimulus. For example, a cardiac wavefront controller may be employed to apply an electrical stimulus to the tissue from two or more different effectors (e.g., present on the same satellites that that were employed in the wave velocity determination) in a manner sufficient to compensate for the region of abnormal depolarization wave conduction. The cardiac wavefront controller may vary, as reviewed in greater detail below, and may apply stimulus sequentially or simultaneously from two or more effectors of two or more satellites.

Specific Illustrative Embodiments

Turning now to the figures, FIG. 1 illustrates the location of a number of satellites in a human heart including a central system 1 (e.g., an implantable cardioverter defibrillator (ICD) or artificial pacemakers can), a right ventricular lead 2, a first satellite 3, a second satellite 4, a left ventricular lead 5, a third satellite 6, a fourth satellite 7, and a pressure sensor 8. Central system 1 provides a centralized communication center and includes a central processing unit, a memory, and several inputs and outputs for communicating between and end user and the satellites. Central system 1 can also be configured for inputting and outputting digital or analog signals and includes an analog to digital converter and a digital to analog converter. Central system 1 can also function as a pacing and signal detection system for controlling a pacemaker with sensors residing in an external or extra-corporeal location.

Right ventricular lead 2 connects central system 1 with first satellite 3, second satellite 4 and pressure sensor 8. The number of satellites and sensors that may be connected to the right ventricular lead 2 is not limited and may be more or less than the number shown in this embodiment. Right ventricular lead 2 runs from central system 1 into the patient's body (e.g., preferably, a subclavian venous access), and through the superior vena cava into the right atrium. From the right atrium, right ventricular lead 2 is threaded through the tricuspid valve to a location along the walls of the right ventricle. The distal portion of right ventricular lead 2 is preferably located along the intra-ventricular septum, terminating with fixation in the right ventricular apex. Right ventricular lead 2 includes bus wires that are coupled to a number of satellites. The number of bus wires included in right ventricular lead 2 is limited only by the size of the lead and wires but is preferably two if a two wire embodiment is used or one if a wire embodiment is used as is further described below with reference to FIG. 3 and FIG. 4. The bus wires are labeled as Si where i=1, 2. Left ventricular lead 5, which connects central system 1 with third satellite 6 and fourth satellite 7, is similar to right ventricular lead 2 except that it is routed through a different part of the heart. Left ventricular lead 5 runs from central system 1 into the patient's body following substantially the same route as right ventricular lead 2 (e.g., through the subclavian venous access and the superior vena cava into the right atrium). From the right atrium, left ventricular lead 5 is threaded through the coronary sinus around the posterior wall of the heart in a cardiac vein draining into the coronary sinus. Left ventricular lead 5 then runs laterally along the walls of the left ventricle, which is a likely position to be advantageous for bi-ventricular pacing. Like right ventricular lead 2, left ventricular lead 5 contains bus wires coupled to satellites.

First satellite 3, second satellite 4, third satellite 6 and fourth satellite 7 are similar to each other except that they are located in different positions and have different identifiers. Identifiers can include an address of the satellite or other means for distinguishing between the different satellites. In one embodiment each satellite 3, 4, 6, 7 includes electrodes configured in the four quadrants of the cylindrical outer walls of satellite, an integrated circuit ("control chip") which communicates with central system 1 to receive configuration signals that determine which of the four electrodes are to be coupled to bus wires. For more details of this configuration, see e.g., PCT Application Serial Nos. PCT/US2005/046811 and PCT/US05/031559; the disclosures of which are herein incorporated by reference.

Pressure sensor 8 is coupled to right ventricular lead 2 and is connected to a bus wire, as are the satellites. Although pressure sensor 8 is shown as located on the right ventricular lead 2 and is used to measure the pressure in the right ventricle, it can be located anywhere along the right ventricular lead 2 or the left ventricular lead 5 and can be used to measure the pressure anywhere it is positioned. The central system can include a signal multiplexing arrangement to accommodate active devices such as the pressure sensor 8.

Figure 2:
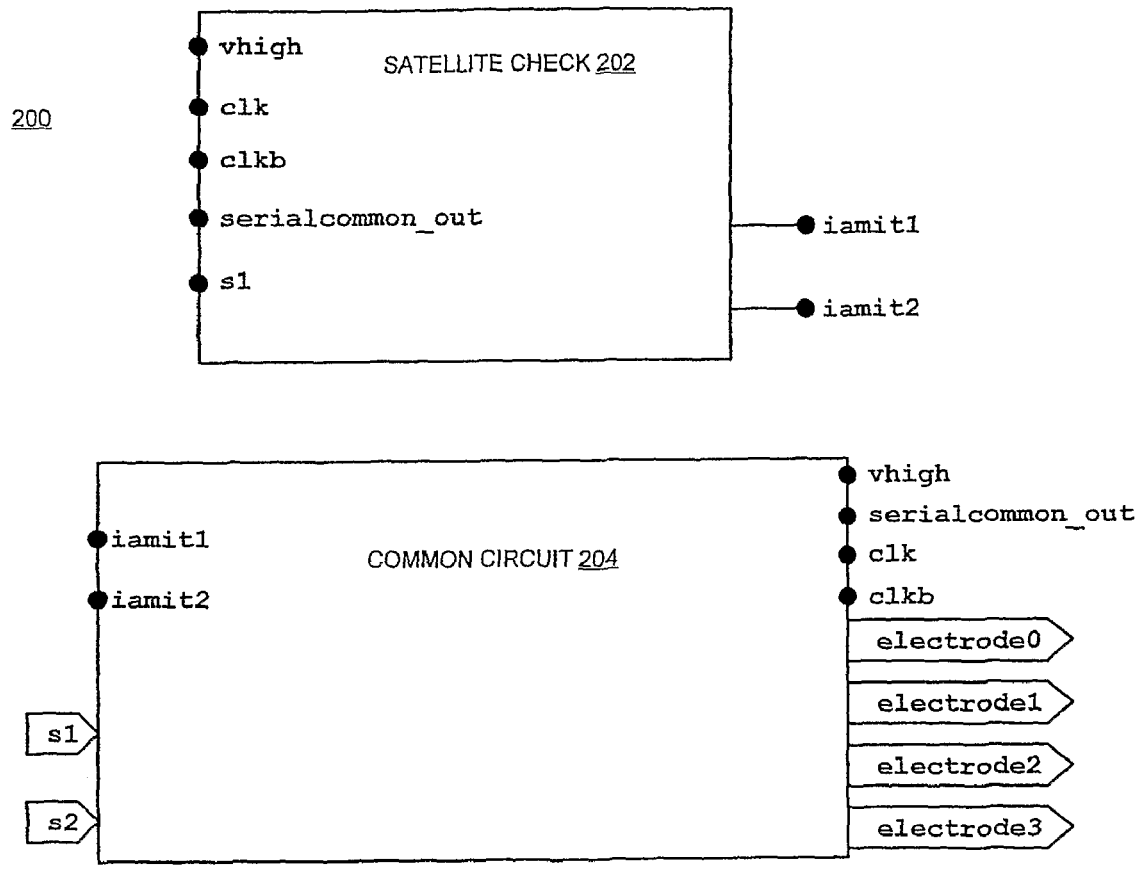
FIG. 2 is a block diagram showing two portions of an integrated circuit ("control chip") in a satellite, in accordance with an embodiment of the present invention.

FIG. 2 is a block diagram 200 showing two portions of an integrated circuit ("control chip") in a satellite including a satellite check 202 and a common circuit 204. Further details of these circuits can be found in copending U.S. patent application Ser. No. 11/219,305 and PCT application serial no. PCT/US2005/031559, which applications have already been incorporated in its entirety by reference. Common circuit 204 is coupled to bus wires S1 and S2 and carries out such functions as deriving power supply signal Vhigh, recovering clock signal "clk" (provided as a pair of complementary clock signals "cclk" and "clkb") and recovering data bits from signal VS2, decoding address signals and control commands, and configuring the electrodes. Common circuit 204 provides decoded address bits serially to satellite-check circuit 202 as a serial output signal "serialcommon_out." Satellite-check circuit 202 compares the address bits received from common circuit 204 to its stored identity information to derive control signals "iamit1" and "iamit2," which indicate whether the received address bits match the identity information stored in satellite-check circuit 202. (Thus, satellite-check circuits 202 of the satellites differ from each other in their respective stored identity information.) As described below, control signals "iamit1" and "iamit2" are used to derive configuration signals to configure the electrodes in a satellite for subsequent pacing or signal detection phases.

In one embodiment of the present invention, customized digital circuits that do not execute software or middle-ware carry out the functions of a control chip mentioned above. Using these customized circuits is advantages because there is lower power consumption and faster response times.

Figure 3:
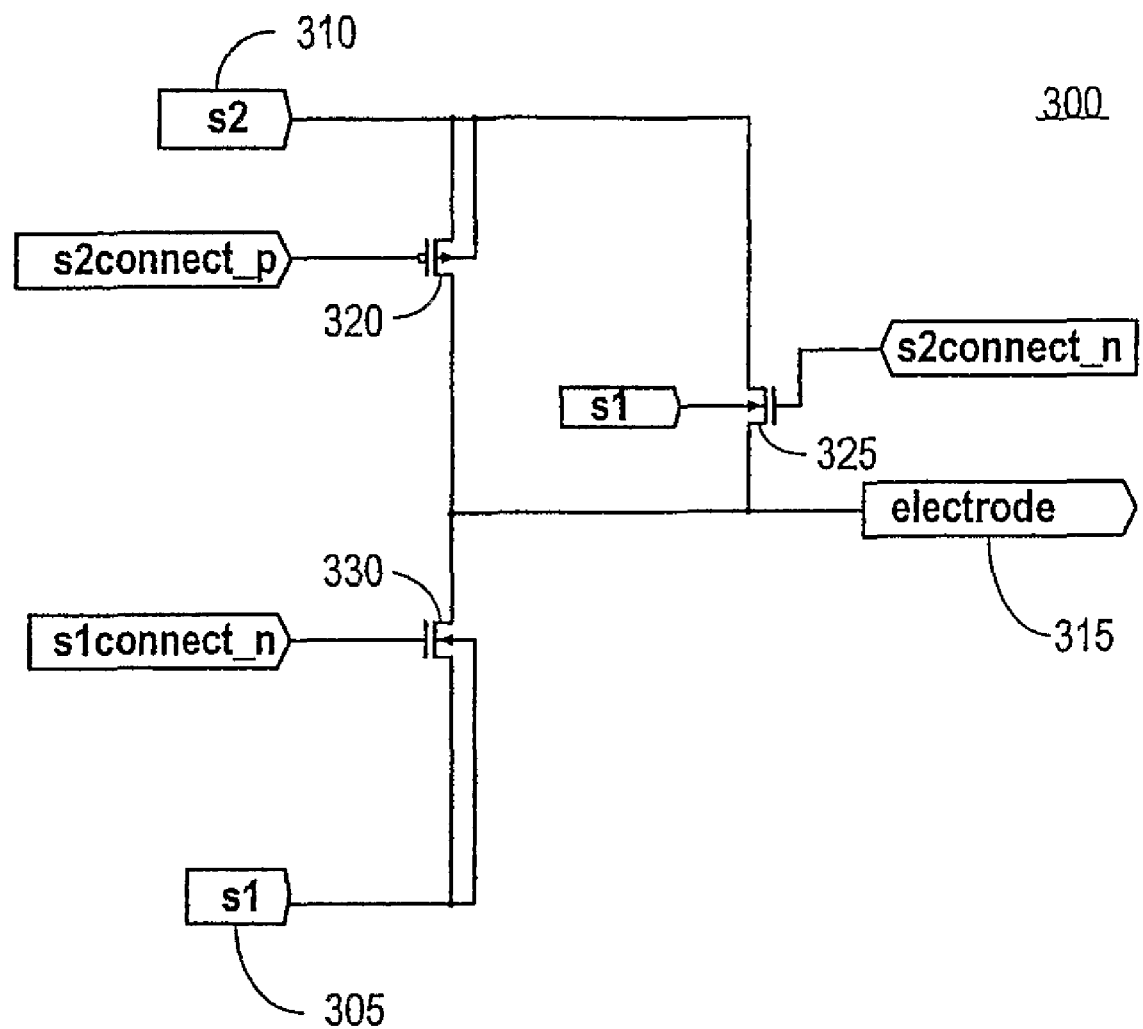
FIG. 3 is a schematic circuit diagram of an electrode control used for detecting a depolarization wave using two wires, in accordance with one embodiment of the invention.

FIG. 3 is a schematic circuit diagram of an electrode control 300 used for detecting a depolarization wave using two wires including a first bus wire (S1) 305, a second bus wire (S2) 310, an electrode 315, a PMOS transistor 320, a first NMOS transistor 325, and a second NMOS transistor 330. In circuit 300, a low voltage at signal "s2connect_p" couples the electrode 315 to second bus wire (S2) 310 through PMOS transistor 320. A high voltage at signal "s2connect_n" couples the electrode 315 to bus second wire (S2) 310 via first NMOS transistor 325. A high voltage at signal "s1connect_n" couples the electrode to first bus wire (S1) 305 via second NMOS transistor 330. Thus, the values (1, 0, 0), (0, 1, 0) and (1, 0, 1) for signal combination ("s2connect_p", "s2connect_n", s1connect_n") decouples the electrode from S1 and S2, couples the electrode to S2, and couples the electrode to S1, respectively. Further details of this circuits can be found in U.S. patent application Ser. No. 11/219,305 and PCT application serial no. PCT/US2005/031559, which applications have already been incorporated in their entirety by reference.

The electrode control 300 described enables several features and functions that can be implemented in a cardiac pacing/signal detection system. For example the system can address and individually pace through the two bus wires residing within a pacing lead. Additionally, the system can collect un-amplified analog signals through the satellite electrodes over the same two wires providing flexibility that is not available in conventional pacing systems. Electrode control 300 can also be used to provide power supply and facilitate digital communication simultaneously over the two bus wires. In one embodiment, the control circuit can extract a DC power supply, derive a clock signal, and capture the PSK-modulated bit sequences at the same time. Furthermore, the special initialization generation circuit ensures that during a power-up period, each satellite is not misconfigured by accident.

Since electrode control 300 can be implemented with special device-level designs that minimize leakage current, electrode control 300 can be made to have very low power consumption. In one embodiment, electrode control circuit 300 can be made using CMOS designs with long gate lengths to minimize leakage current through the gates. Additionally, the control circuit may have extra substrate contacts. These low-leakage-current design features enable a control circuit that can be turned off between two consecutive recharges while the circuit remains in a configured state.

Figure 4:
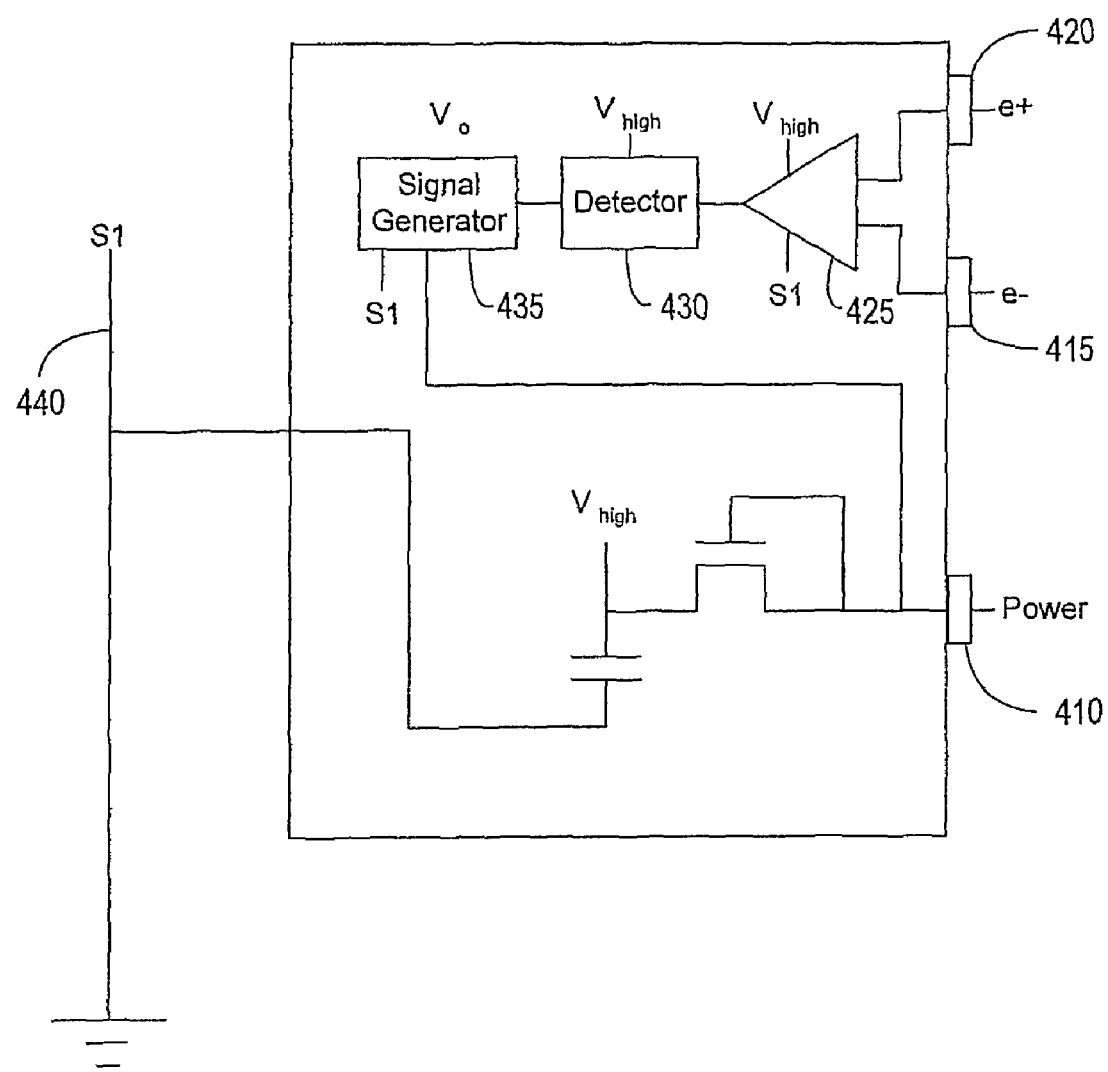
FIG. 4 is a schematic circuit diagram of an electrode control used for detecting a depolarization wave using one wire, in accordance with one embodiment of the invention.

FIG. 4 is a schematic circuit diagram of an electrode control used for detecting a depolarization wave using one wire including a power input 410, an electrode e− input 415, an electrode e+ input 420, an operational amplifier 425, a detector 430, a signal generator 435, and a bus wire (S1) 440. Power input 410 is coupled to the body and receives power through a pulse transmitted through the tissue of the body. Electrode e− input 415 and electrode e+ input 420 make up a bipolar electrode that can be used to detect electrical signals in the body such as a depolarization wave. Operational amplifier 425 receives an electrode e− input 415 and an electrode e+ input 420, compares the two inputs, and outputs a value depending on that comparison. Detector 430 detects the output from operational amplifier 425 and conveys that it has detected a signal to the signal generator 435. Signal generator 435 then transmits a signal through bus wire S1 440 out of the body and to the central system.

This embodiment enables the system with only one-wire instead of the two wire system discussed above with reference to FIG. 3. This one wire system takes advantage of the body's conductive properties and uses them to transmit electrical power and signals through the body. Since power input 410 is connected directly to the tissue of the body and the body is a conductor, power and electrical signals are transmitted through the body and through power input 410 to power the device.

Figure 5:
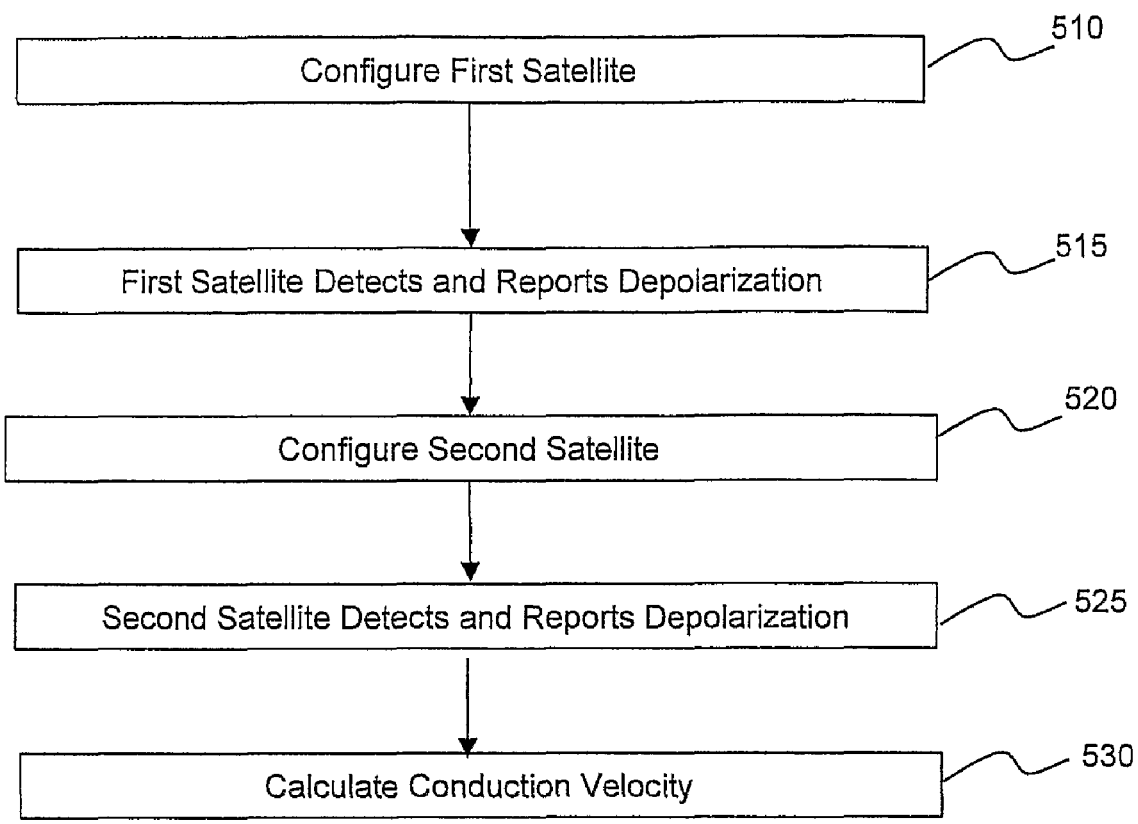
FIG. 5 is a flowchart showing the central system steps used to detect a depolarization wave and measure the conduction velocity of the depolarization wave in accordance with one embodiment of the invention.

FIG. 5 is a flowchart showing the steps used to detect a depolarization wave and measure the conduction velocity of the depolarization wave in accordance with one embodiment of the invention. In the embodiment depicted in FIG. 5, the methods include a step of configuring a first and second satellite to function in the method as desired. In step 510 a first satellite located within the heart is configured to detect and report the presence of a depolarization wave. In step 515, the first satellite detects and reports the presence of the depolarization wave. At step 520, a second satellite also located within the heart but a distance away from the first satellite is configured to detect and report the presence of the same depolarization wave. In step 525 the second satellite detects and reports the presence of the depolarization wave. Since the first satellite and the second satellite are located at different positions in the heart, they will each detect the depolarization wave at different times. In step 530, the conduction velocity is calculated using information about detected waves. In one embodiment, the conduction velocity is calculated by first determining the time difference between when the two satellites detected the depolarization wave and then dividing the known distance between the two satellites and this time difference.

In another embodiment, the conduction velocity in the tissue of a body is measured by first externally stimulating the tissue in the body to generate the depolarization wave to be measured and then using a central system and one satellite at a time that is configured as an electrode with two wires. The central system sends a first configuration signal to a first satellite and a first coupling signal to the first satellite instructing the first satellite to couple a first pair of electrodes to a pair of conductors. After the central system receives a first depolarization signal from the first pair of electrodes, it sends a first decoupling signal to the first satellite to decouple the first pair of electrodes from the pair of conductors. The central system then sends a second configuration signal to a second satellite, which is located a distance away from the first satellite, and sends a second coupling signal to the second satellite instructing the second satellite to couple a second pair of electrodes to the pair of conductors. After the central system receives a second depolarization signal from the second pair of electrodes, it sends a second decoupling signal to the second satellite to decouple the second pair of electrodes from the pair of conductors. Finally the central system determines a time interval between the first depolarization signal and the second depolarization signal and calculates the conduction velocity using said time interval and the distance. In conjunction, the satellite receives from the central system a configuration signal and a signal to couple a pair of electrodes to a pair of conductors. The satellite then couples a pair of electrodes to a pair of conductors so that electrodes are directly coupled to the central system and signals received by the satellite are directly communicated to the central system. Finally, the satellite receives a signal to decouple the pair of electrodes from the pair of conductors and does so. A second satellite is then engaged and follows the same steps as the first satellite.

Figure 6A:
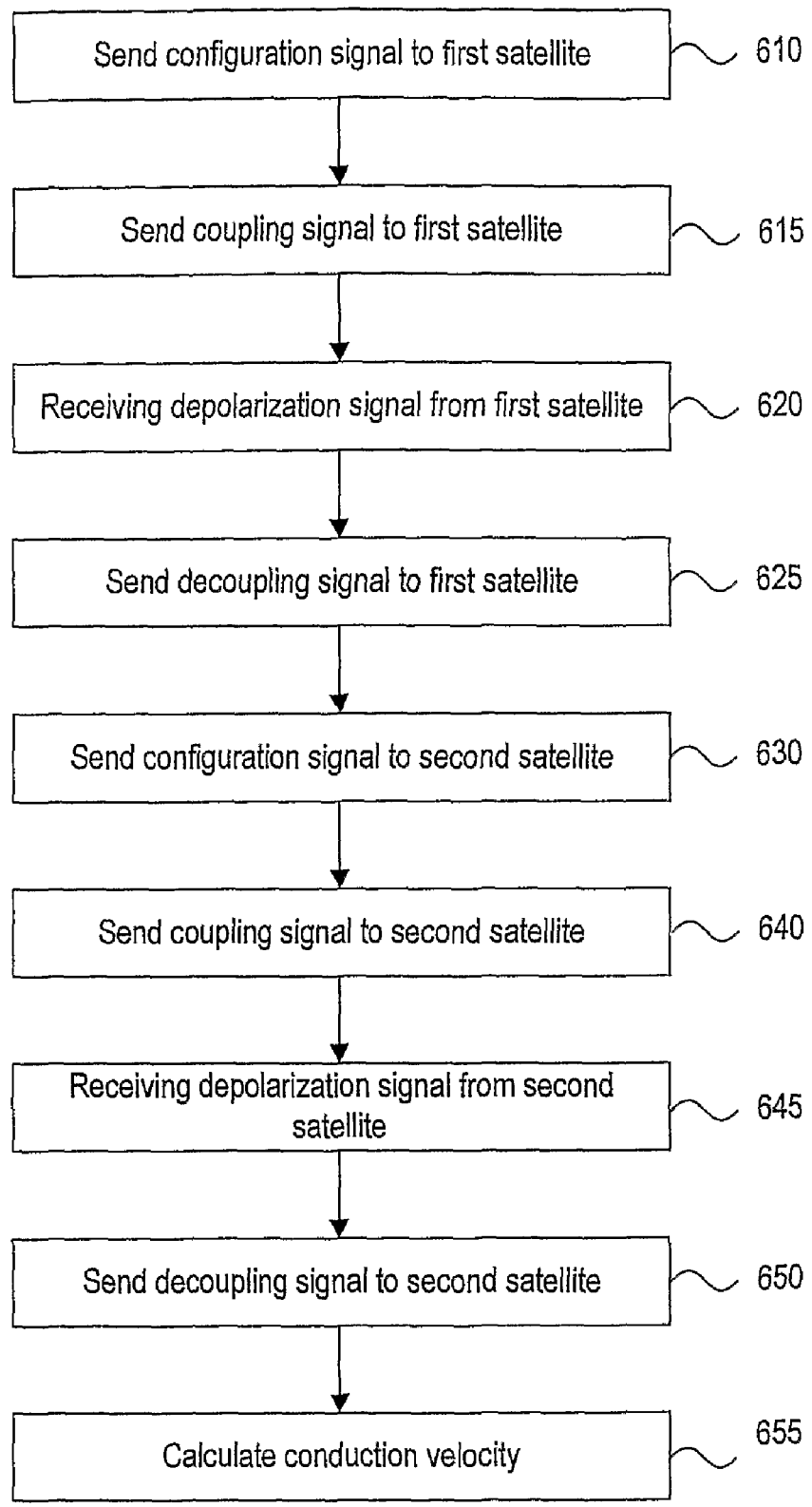
FIG. 6A is a flowchart showing the central system steps used to detect a depolarization wave, which has been externally stimulated, and measure the conduction velocity of the depolarization wave using one satellite at a time that is configured as an electrode with two wires, in accordance with one embodiment of the invention.

FIG. 6A is a flowchart showing the central system steps used to detect a depolarization wave, which has been externally stimulated, and measure the conduction velocity of the depolarization wave using one satellite at a time that is configured as an electrode with two wires, in accordance with one embodiment of the invention. First in step 610 the central system sends a configuration signal to a first satellite. The configuration signal communicates to the satellite information such as the satellite address, which electrodes to couple to use, etc. Next in step 615 and after the first satellite has been configured, the central system sends a coupling signal to the first satellite instructing the first satellite to couple a pair of electrodes to a pair of conductors. This step transforms the first satellite into a transducer that is ready to detect an electrical signal produced by a depolarization wave. In an alternative embodiment steps 610 and 615 can be combined so that the configuration signal and the coupling signal are sent together in one step.

Next in step 620 the central system receives a first depolarization signal from the pair of electrodes configured on the first satellite. The first depolarization signal transmitted by the first satellite is the voltage measured by the pair of electrodes in the first satellite. Other embodiments can transmit depolarization signals that are more complex than just the measured voltage such as digitized signals or time derivatives of voltages. The central system records the signal along with other information such as the time it received the signal and the satellite that sent the signal. After receiving the depolarization signal, the central system sends a decoupling signal in step 625 to the satellite causing the satellite to decouple its pair of electrodes from the pair of conductors. Next in step 630 the central system sends a configuration signal to a second satellite. The configuration signal communicates to the second satellite similar information communicated to the first satellite. In step 640 and after the second satellite has been configured, the central system sends a coupling signal to the second satellite instructing the second satellite to couple a pair of its electrodes to the same pair of conductors that the electrodes of the first satellite were coupled. Steps 630 and 640 are similar to steps 610 and 615 respectively except that a different satellite is being configured and coupled. In step 645 the central system receives a second depolarization signal from the pair of electrodes configured on the second satellite. The second depolarization signal is similar to the first depolarization signal except that the second satellite instead of the first satellite transmitted it. The central system records the second depolarization signal along with other information such as the time it received the signal and the satellite that sent the signal and afterwards sends a decoupling signal in step 650 to the second satellite causing the second satellite to decouple its pair of electrodes from the pair of conductors.

Next in step 650 the central system calculates the conduction velocity. In this embodiment the conduction velocity is calculated by first determining a time interval between the first depolarization signal and the second depolarization signal. The central system can do this by comparing the recorded times of the first depolarization signal and second depolarization signal. Once the time interval is determined the conduction velocity is calculated using the known distance between the satellites and this time interval. A simple model for the velocity is this known distance divided by the time interval.

Figure 6B:
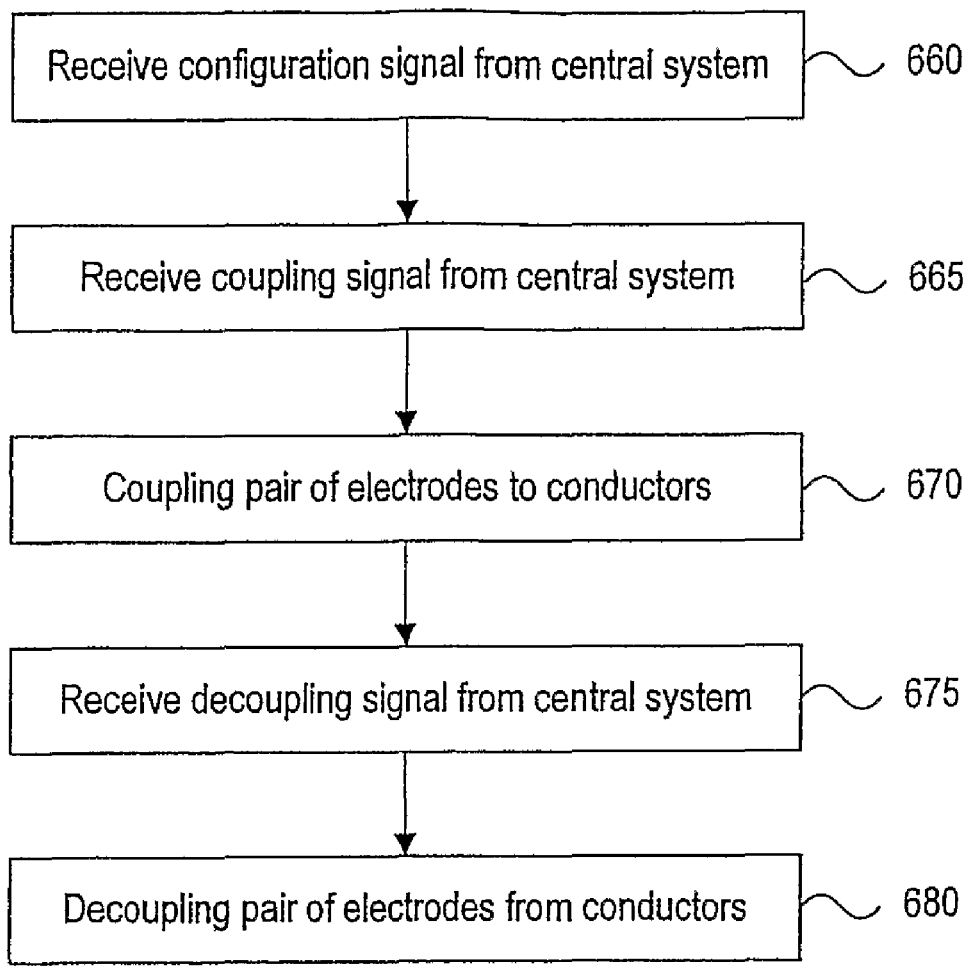
FIG. 6B is a flowchart showing the satellite steps corresponding to the central system steps of FIG. 6A.

FIG. 6B is a flowchart showing the satellite steps corresponding to the central system steps of FIG. 6A used to detect a depolarization wave, which has been externally stimulated, and measure the conduction velocity of the depolarization wave using one satellite at a time that is configured as an electrode with two wires, in accordance with one embodiment of the invention. First in step 660 the satellite receives a configuration signal from the central system, which was sent in step 610. In step 665 the satellite receives a coupling signal to couple a pair of electrodes to a pair of conductors, which was sent in step 615. Next in step 670 the satellite couples a pair of electrodes to a pair of conductors so that electrodes are directly coupled to the central system and signals received by the satellite are directly communicated to the central system. In step 675 the satellite receives a decoupling signal to decouple the pair of electrodes from the pair of conductors, which was sent in step 625. Finally in step 680 the satellite decouples the pair of electrodes from the pair of conductors so that electrodes no longer transmit information to the central system.

In another embodiment, the conduction velocity in the tissue of a body is measured by first externally stimulating the tissue in the body to generate the depolarization wave to be measured and then using a central system and one satellite at a time that is configured to be smart. The central system sends a first configuration signal to a first satellite, and then after receiving a first depolarization signal from the first satellite, sends a second configuration signal to a second satellite located a distance away from the first satellite. After the central system receives a second depolarization signal from the second satellite, it determines a time interval between the first depolarization signal and said second depolarization signal, and calculates the conduction velocity using the time interval and the distance. In conjunction, the satellite receives a configuration signal from the central system, couples an electrode to a conductor, detects the polarization wave, communicates a signal to the central system representing the detection of a depolarization wave, and decouples the electrode from the conductor.

Figure 7A:
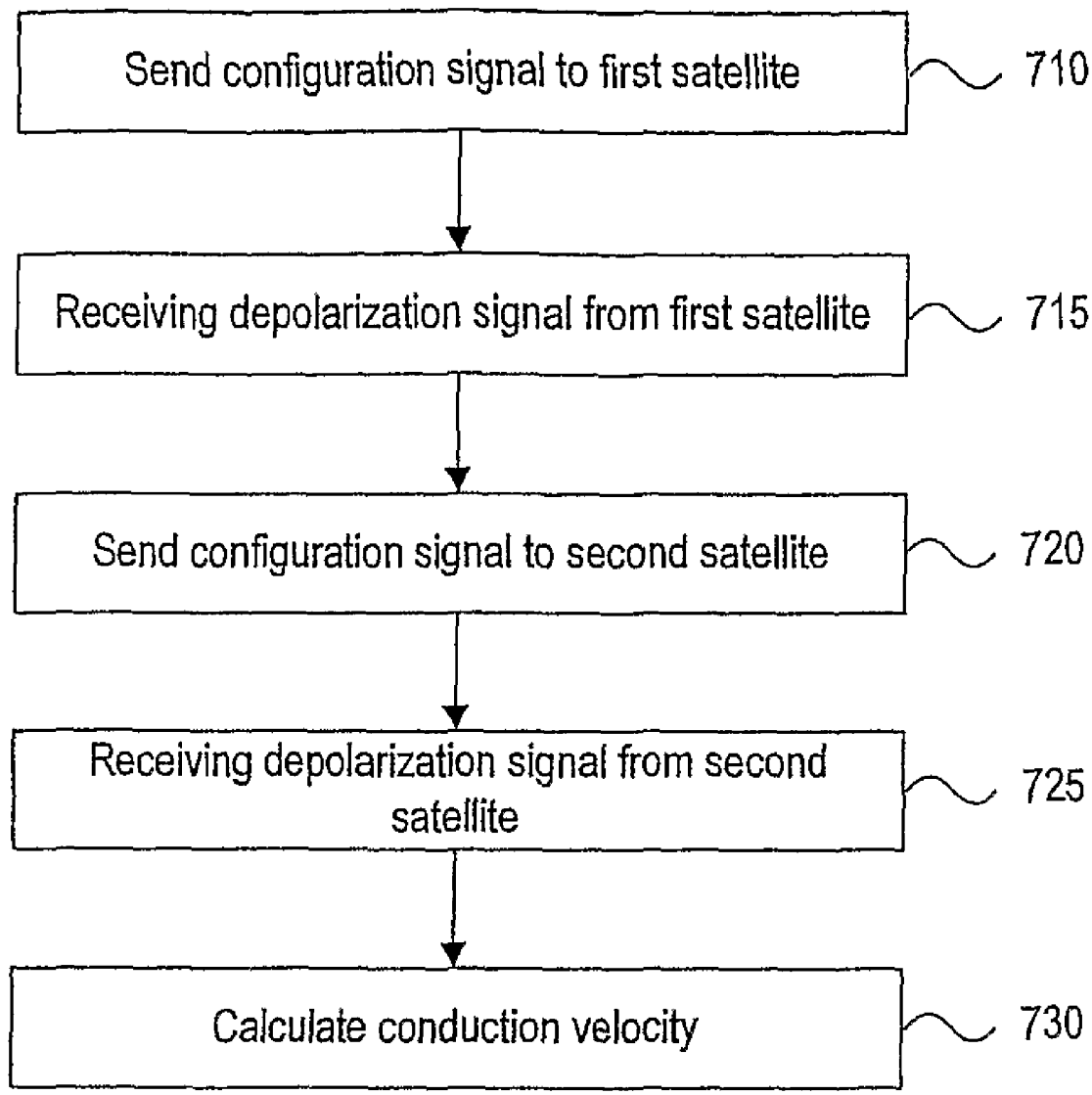
FIG. 7A is a flowchart showing the central system steps used to detect a depolarization wave, which has been externally stimulated, and measure the conduction velocity of the depolarization wave using one satellite at a time that is configured to be smart, in accordance with one embodiment of the invention.

FIG. 7A is a flowchart showing the central system steps used to detect a depolarization wave, which has been externally stimulated, and measure the conduction velocity of the depolarization wave using one satellite at a time that is configured to be smart, in accordance with one embodiment of the invention. This embodiment can be either implemented using the two-wire configuration described with reference to FIG. 3 above or the one-wire configuration described with reference to FIG. 4 above. First in step 710 the central system sends a configuration signal to a first satellite. The configuration signal communicates to the satellite information such as the satellite address, which electrodes to couple to use, etc. Next in step 715 the central system receives a first depolarization signal from the first satellite. The first depolarization signal transmitted by the first satellite can be analog or digital depending on how the satellite is equipped. Although the satellite measures an analog signal it may be equipped with circuitry including an analog to digital converter, filters, amplifiers that process the measured signal before transmitting it. The depolarization signal transmitted by the satellite may also include other information such as addresses, satellite identifiers, or time stamps. The central system records the transmitted depolarization signal along with other information, which can include the time it received the signal and the satellite that sent the signal. After receiving the depolarization signal, the central system sends a configuration signal in step 720 to a second satellite. The configuration signal communicates to the second satellite similar information communicated to the first satellite in step 710. In step 725 the central system receives a second depolarization signal from the second satellite. The second depolarization signal is similar to the first depolarization signal except that the second satellite instead of the first satellite transmitted it. The central system records the second depolarization signal along with other information such as the time it received the signal and the satellite that sent the signal. Finally, in step 730 the central system calculates the conduction velocity. In this embodiment the conduction velocity can be calculated in the same way it was calculated in step 650 above. However, since this embodiment includes satellites that have the ability to transmit additional information including time and satellite identification along with a representation of the measured voltage the central system can calculate the conduction velocity using these parameters as well. A representation can include the voltage generated by the electrodes when it senses the depolarization wave, an amplified voltage, a digitized voltage or other value which can be used to identify the depolarization wave.

Figure 7B:
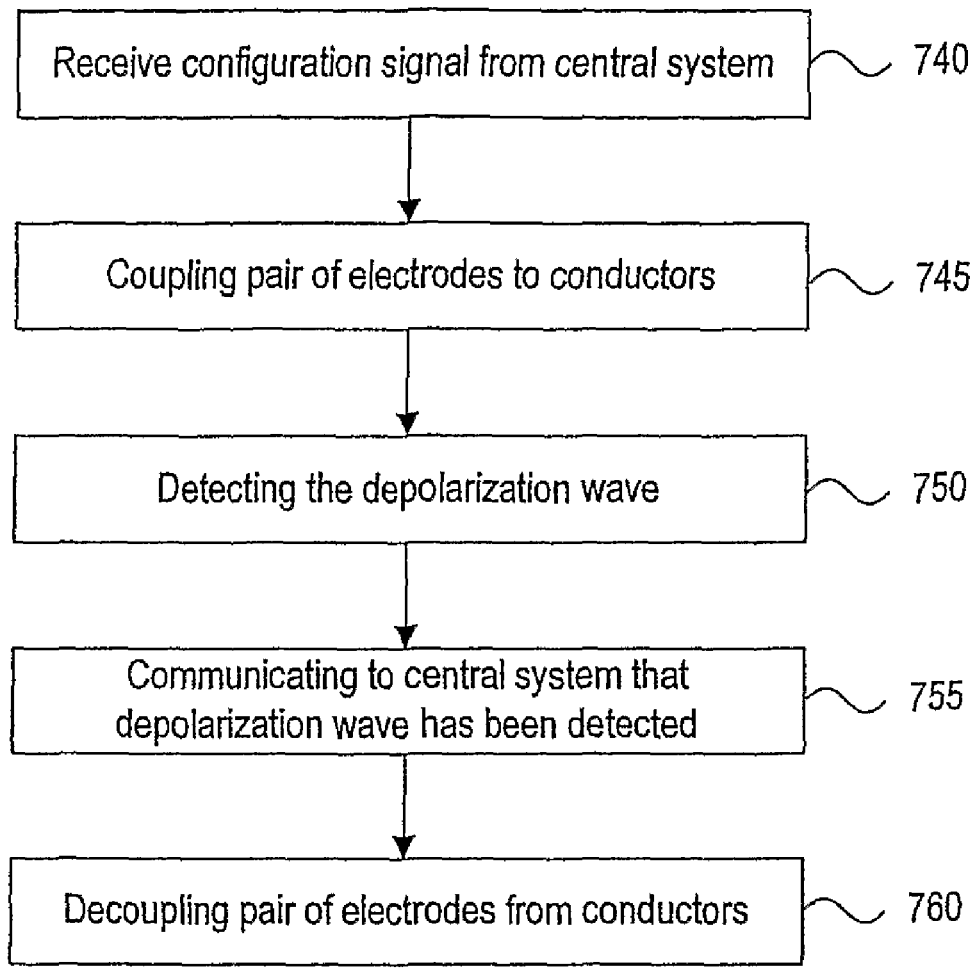
FIG. 7B is a flowchart showing the satellite steps corresponding to the central system steps of FIG. 7A.

FIG. 7B is a flowchart showing the satellite steps corresponding to the central system steps of FIG. 7A used to detect a depolarization wave, which has been externally stimulated, and measure the conduction velocity of the depolarization wave using one satellite at a time that is configured to be smart, in accordance with one embodiment of the invention. First in step 740 the satellite receives a configuration signal from the central system, which was sent in step 710. Next in step 745 the satellite couples a pair of electrodes to a pair of conductors so that electrodes can detect the depolarization wave. In step 750 the electrodes detect the depolarization wave. Next in step 755 the satellite communicates to the central system that it has detected a depolarization wave. The central system receives this communication as the depolarization signal in step 715. As described above with reference to step 715 this communication can be analog or digital and can contain information such as addresses, satellite identifiers, or time stamps. Finally in step 760 the satellite decouples the pair of electrodes from the pair of conductors so that electrodes no longer transmit information to the central system.

In another embodiment, the conduction velocity in the tissue of a body is measured by first externally stimulating the tissue in the body to generate the depolarization wave to be measured and then using a central system and two satellites at the same time that are configured to be smart. The central system sends a first configuration signal to a first satellite, sends a second configuration signal to a second satellite after the first configuration signal is sent but before a depolarization wave is detected by the first satellite and reaches the second satellite. The central system then receives a first depolarization signal from the first satellite and a second depolarization signal from the second satellite respectively when each satellite detects the depolarization wave. Consequently, the central system determines a time interval between the first depolarization signal and the second depolarization signal, and calculates the conduction velocity using the time interval and the distance. In conjunction, both the first satellite and the second satellite each receive a configuration signal from the central system, coupling an electrode to a conductor, detect the polarization wave, communicate a signal to the central system representing the detection of a depolarization wave, and decouple their electrodes from the conductor once they have communicated to the central system.

Figure 8:
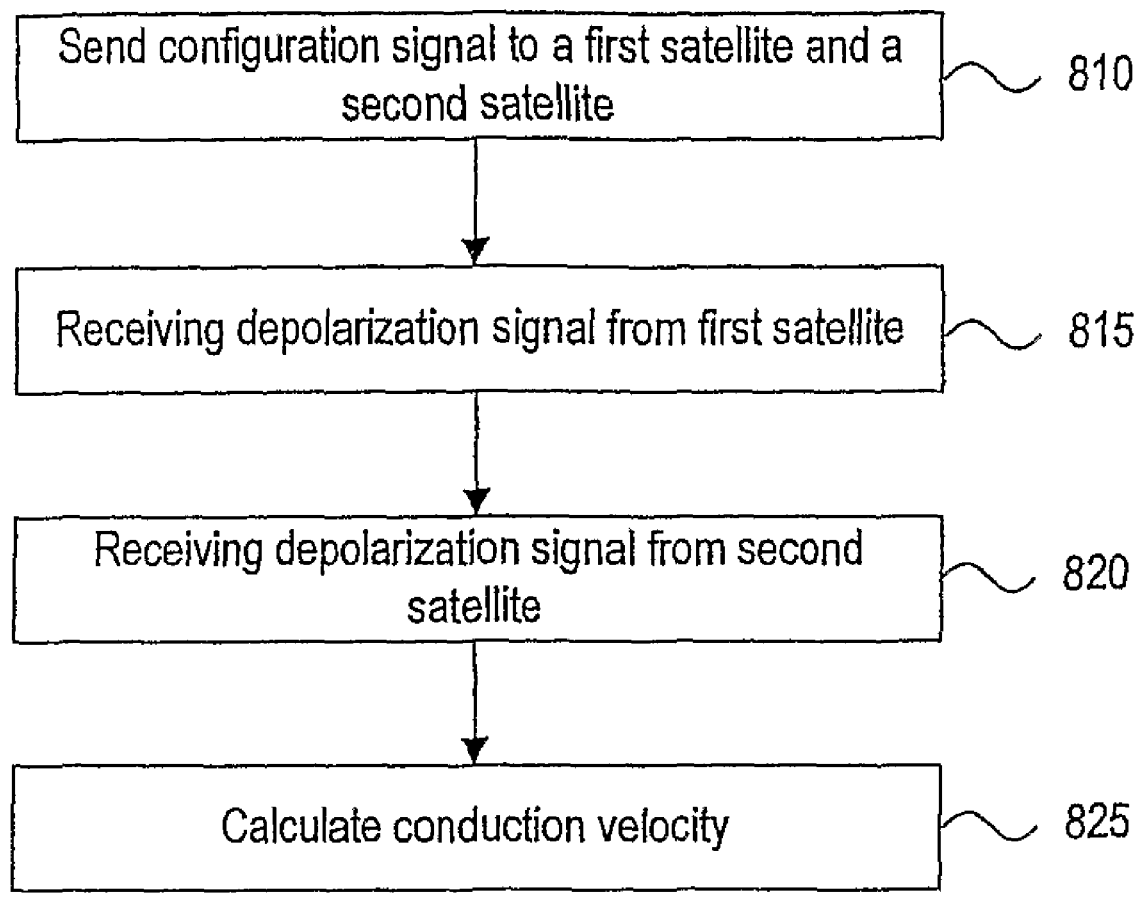
FIG. 8 is a flowchart showing the central system steps used to detect a depolarization wave, which has been externally stimulated, and measure the conduction velocity of the depolarization wave using two satellites at the same time that are configured to be smart, in accordance with one embodiment of the invention.

FIG. 8 is a flowchart showing the central system steps used to detect a depolarization wave, which has been externally stimulated, and measure the conduction velocity of the depolarization wave using two satellites at the same time that are configured to be smart, in accordance with one embodiment of the invention. This embodiment can be either implemented using the two-wire configuration described with reference to FIG. 3 above or the one-wire configuration described with reference to FIG. 4 above. First in step 810 the central system sends a configuration signal to a first satellite and a second satellite. The configuration signal communicates to the satellite information such as the satellite address, which electrodes to couple to use, etc. In one embodiment the configuration signal sent to the first satellite can be sent first and the configuration signal sent to the second satellite can be sent later but before a depolarization wave is detected by the first satellite and reaches the second satellite. Next in step 815 the central system receives a first depolarization signal from the first satellite. A short time after receiving first depolarization signal from the first satellite, the central system receives a second depolarization signal from the second satellite in step 820. Both the first depolarization signal and the second depolarization signal transmitted by the first satellite and second satellite can be analog or digital depending on how the satellite is equipped and preferably contain other information such as addresses, satellite identifiers, or time stamps. The central system records the first transmitted depolarization signal and the second transmitted depolarization signal along with other information which can include the time it received the signal and the satellite that sent the signal in steps 815 and 820 respectively. Finally, in step 825 the central system calculates the conduction velocity. In this embodiment the conduction velocity can be calculated in the same way it was calculated in step 730 above.

The satellite steps corresponding to the central system steps of FIG. 8 are similar to those of the satellite steps discussed with reference to FIG. 7B above. Therefore a flowchart showing the satellite steps corresponding to the central system steps of FIG. 8 is omitted.

In another embodiment, the conduction velocity in the tissue of a body is measured by first internally stimulating the tissue in the body to generate the depolarization wave to be measured and then using a central system and two satellites configured as electrodes connected with two wires. The central system sends a first configuration signal to a first satellite, then sends a first coupling signal to the first satellite instructing the first satellite to couple a first pair of electrodes to a pair of conductors, then sends a signal to stimulate the tissue to create a depolarization wave and records when it was sent, and then sends a first decoupling signal to the first satellite to decouple the first pair of electrodes from the pair of conductors. The central system then sends a second configuration signal to a second satellite located a distance away from said first satellite, then sends a second coupling signal to the second satellite instructing the second satellite to couple a second pair of electrodes to the pair of conductors. The central system then receives a depolarization signal from the second pair of electrodes, sends a second decoupling signal to the second satellite to decouple the second pair of electrodes from the pair of conductors, determines a time interval between when the stimulation occurred and when the second depolarization signal was received, and calculates the conduction velocity using the time interval and the distance. In conjunction, the satellite used as a stimulator receives a configuration signal and a signal to couple a pair of electrodes to a pair of conductors from the central system, stimulates the tissue to generate a depolarization wave, and then decouples the pair of electrodes from the pair of conductors. The satellite, which is used as a sensor, receives from the central system a configuration signal and a signal to couple a pair of electrodes to a pair of conductors. This satellite then couples a pair of electrodes to a pair of conductors so that electrodes are directly coupled to the central system and signals received by the satellite are directly communicated to the central system. Finally, the satellite receives a signal to decouple the pair of electrodes from the pair of conductors and does so.

Figure 9A:
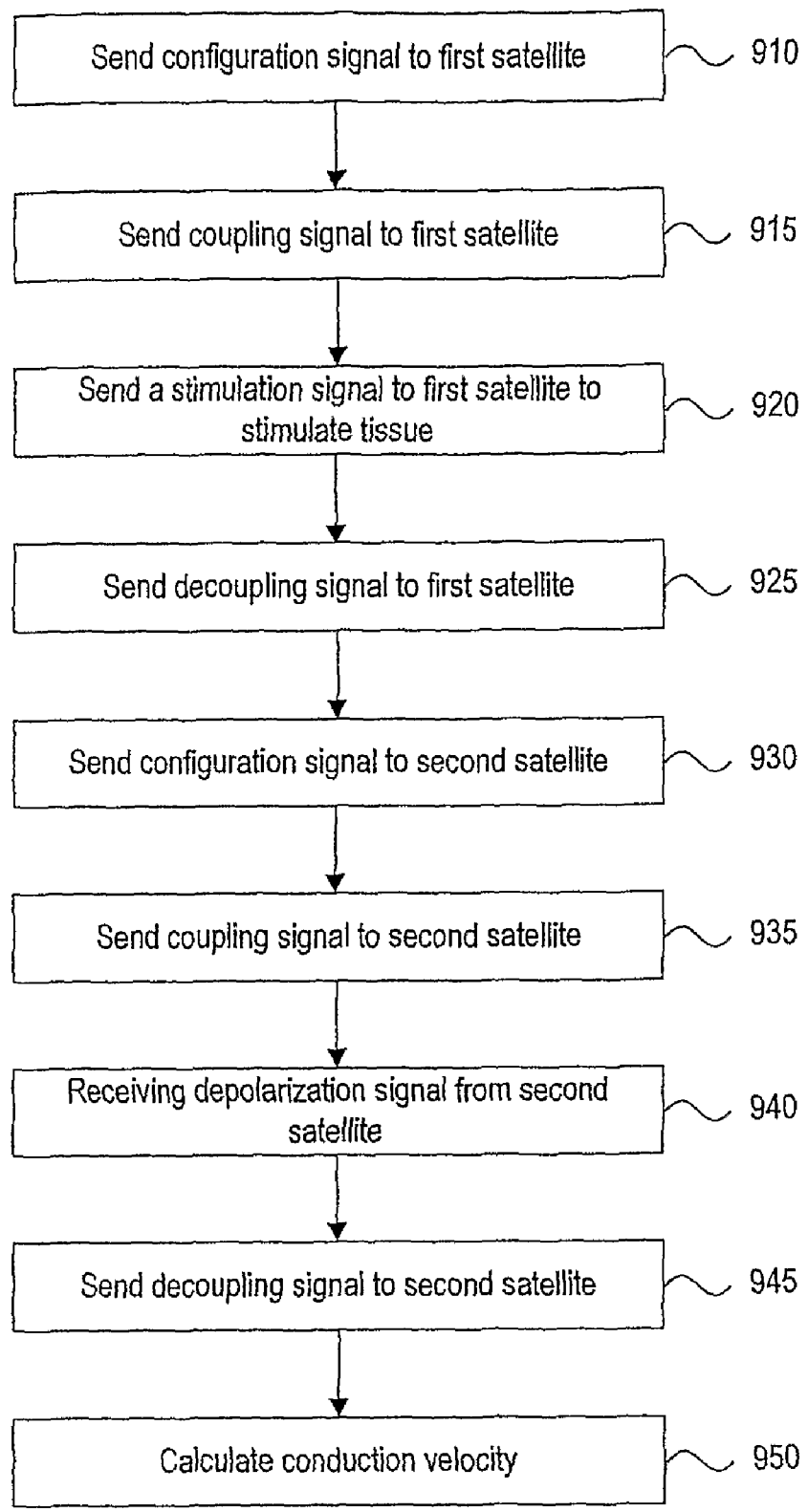
FIG. 9A is a flowchart showing the central system steps used to detect a depolarization wave, which has been internally stimulated, and measure the conduction velocity of the depolarization wave using two satellites configured as electrodes with two wires, in accordance with one embodiment of the invention.

FIG. 9A is a flowchart showing the central system steps used to detect a depolarization wave, which has been internally stimulated, and measure the conduction velocity of the depolarization wave using two satellites configured as electrodes with two wires, in accordance with one embodiment of the invention. First in step 910 the central system sends a configuration signal to a first satellite. The configuration signal communicates to the satellite information such as the satellite address, which electrodes to couple to use, etc. Next in step 915 and after the first satellite has been configured, the central system sends a coupling signal to the first satellite instructing the first satellite to couple a pair of electrodes to a pair of conductors. This step transforms the first satellite into a stimulator that is ready to stimulate the surrounding tissue with an electrical pulse to generate a depolarization wave that can be detected. In one embodiment the stimulator is an electrode configured to deliver an electrical pulse. In an alternative embodiment, steps 910 and 915 can be combined so that the configuration signal and the coupling signal are sent together in one step.

Next in step 920 the central system sends a stimulation signal to the first satellite. The stimulation signal transmitted to the first satellite is preferably a voltage of sufficient strength to generate a depolarization wave in the tissue that will propagate throughout the tissue. The stimulation signal is preferably a voltage pulse of several millivolts lasting for approximately several milliseconds. In addition to sending a stimulation signal, the central system also records information about the stimulation signal such as time sent, which satellite received the stimulation signal, voltage of the signal, and duration of the signal. Next in step 925 the central system sends a decoupling signal to the first satellite causing the satellite to decouple its pair of electrodes from the pair of conductors. In step 930 the central system sends a configuration signal to a second satellite. The configuration signal communicates to the second satellite similar information communicated to the first satellite. In step 935 and after the second satellite has been configured, the central system sends a coupling signal to the second satellite instructing the second satellite to couple a pair of its electrodes to the same pair of conductors that the electrodes from the first satellite were previously coupled to. Steps 930 and 935 are similar to steps 910 and 915 respectively except that a different satellite is being configured and coupled. In step 940 the central system receives a depolarization signal from the pair of electrodes configured on the second satellite. The depolarization signal transmitted by the second satellite is the voltage measured by the pair of electrodes in the second satellite. Other embodiments can transmit depolarization signals that are more complex than just the measured voltage such as digitized signals or time derivatives of voltages. The central system records the signal along with other information such as the time it received the signal and the satellite that sent the signal. After receiving the depolarization signal, the central system sends a decoupling signal in step 945 to the second satellite causing the second satellite to decouple its pair of electrodes from the pair of conductors.

Next in step 950 the central system calculates the conduction velocity. In this embodiment the conduction velocity is calculated by first determining a time interval between when the stimulation signal was sent and when the depolarization wave was detected. The central system can do this by comparing the recorded times of the stimulation signal and the depolarization signal. Once the time interval is determined the conduction velocity is calculated using the known distance between the satellites and this time interval. A simple model for the velocity is this known distance divided by the time interval.

Figure 9B:
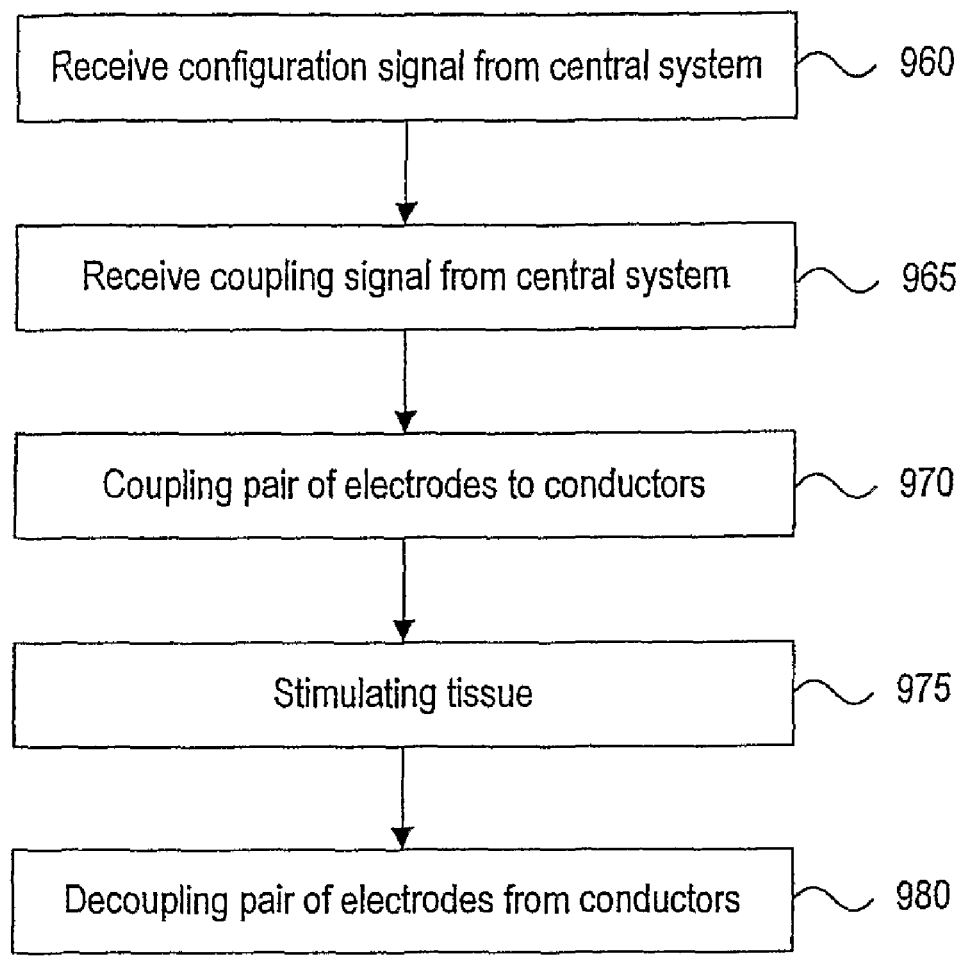
FIG. 9B is a flowchart showing the satellite steps corresponding to the central system steps of FIG. 9A.

The embodiment of FIG. 9B uses a first satellite which is configured as a stimulator and a second satellite which is configured as a detector. The satellite steps of the second satellite, which is configured as a detector, corresponding to the central system steps of FIG. 9A are similar to those of the satellite steps discussed with reference to FIG. 7B above. Therefore a flowchart showing the satellite steps of the second satellite corresponding to the central system steps of FIG. 9A is omitted.

FIG. 9B is a flowchart showing the satellite steps of the first satellite used as stimulator corresponding to the central system steps of FIG. 9A. First in step 960 the satellite receives a configuration signal from the central system, which was sent in step 910. In step 965 the satellite receives a coupling signal to couple a pair of electrodes to a pair of conductors, which was sent in step 915. Next in step 970 the satellite couples a pair of electrodes to a pair of conductors so that electrodes are directly coupled to the central system. In step 975 the satellite stimulates the tissue by applying a voltage to the tissue that is sent by the central system in step 920. Finally in step 980 the satellite decouples the pair of electrodes from the pair of conductors so that electrodes are isolated from the central system.

The depolarization wave conduction velocity data and processed versions thereof, e.g., direction data (both two- and three-dimensional) may be used for a variety of different applications, including both diagnostic and therapeutic applications, where certain of these applications are reviewed in greater detail below. For example, the data obtained using the subject devices and systems may be employed to detection regions of abnormal depolarization wave conductivity, and thereby better diagnose the presence of a cardiac disease condition. The data obtained using the subject devices and systems may also be employed in determining the best therapy to provide to a patient, e.g., pharmacological, electrical or combination thereof. In certain embodiments, the same system that is employed to obtain the data regarding depolarization wave conduction velocity may be employed to apply electrical (e.g., pacing) therapy to the patient.

Cardiac Wavefront Controller

Of interest in certain embodiments is the use of a cardiac wavefront controller to apply the appropriate therapy to the subject following detection of the presence of an abnormality. As indicated further below, the following cardiac wavefront controller technology is described in the present application as one type of therapy that can be applied following detection of a region of abnormal conduction by the subject methods. However, the cardiac wavefront controller technology can readily be employed with other methods of detecting regions of abnormal conductivity. As such, the use of cardiac wavefront controller technology to correct for abnormal conductivity in a region of tissue is not limited to embodiments where regions of abnormal conductivity are detected using the protocols, e.g., as reviewed above.

As summarized above, the cardiac wavefront controller of these embodiments provides an interactive, low voltage treatment for abnormalities in wave propagation, which can manifest as atrial fibrillation, atrial flutter and arrhythmias. The treatment is provided by multiple electrode leads or array patches developed by some of the present inventors, as shown in the patent applications incorporated herein, as referenced above.

In these embodiments, the multielectrode lead or array patch is positioned in the heart or near the heart. The multiple electrodes on these devices are activated in a specific manner to break the spasmodic effect of electrical pulses in the heart that leads to fibrillation and flutter. The strategy for the activation, including timing, energy level, electrode satellite and segment selection, and activation order can be facilitated by information obtained by local sensors on the lead. In some case these sensors are the electrodes functioning in a dual capacity. Preset software "scripts" of these strategies can be employed to optimize results and minimize instillation time and cost.

In addition to linear electrode arrays, the cardiac wavefront controller in some embodiments employs a mesh of electrodes. This mesh of electrodes, which may include a full "heart sock" or a heart patch, as referenced below.

The cardiac wavefront controller may be installed in or near the atrium or pericardial space. Alternately, it may be installed over the left ventricle to the cardiac vein or in the right ventricle. A single lead embodiment of a cardiac wavefront controller can be provided with a few to dozens of electrodes. These multiple electrodes provide various points of contact with cardiac structures.

When atrial defibrillation or other forms of tachycardia occur, the cardiac wavefront controller can provide a line of stimulation to the cardiac tissues in need thereof. These stimulations can be so configured to appear either simultaneously or sequentially with the natural heart function. These stimulations are provided for the purpose of forcing the heart into a single condition, allowing the natural sinus rhythm to emerge. In a sense, this treatment could be viewed as a low energy form of defibrillation.

One purpose of the cardiac wavefront controller is, employing multiple stimulation points, to create an alternate wave that reverses the chaos that is going on in these various tachycardia conditions. The heart is forced into a single depolarized state so that its various tissues can immerge in a normal sinus rhythm manner.

A number of different software approaches and algorithms can be employed with the multiple electrode leads. The simplest would be to utilize existing algorithms, which would be applicable where all of the electrodes are simultaneously engaged and stimulated. In this case, all the tissues are receiving the same signal at the same. Applicable algorithms would include the well-known 50 Hz method.

Another embodiment of the cardiac wavefront controller use is to delay the stimulation. The electrodes would then be reprogrammed so that there is some number of μsec delay between them. In this manner, a wavefront propagates from one location and expands over the heart surface. In one example, the electrical stimulation is started near the right atrium. The wave of stimulated electrodes is programmed to propagate over the right atrium, right ventricle, and over the left ventricle.

An alternative treatment approach using the cardiac wavefront controller is to have the center of stimulation be the apex of the heart and have a retrograde line propagate towards the right atria. In this manner, it is ensured that wherever depolarization occurs is covered or stimulated against.

One aspect of treatment using the cardiac wavefront controller is to have many more electrodes that can fire independently, but in some coordinated way with each other or an uncoordinated way with a pathology condition of the heart.

Another treatment approach using the cardiac wavefront controller is to have electrodes fire somewhat randomly in such a way that the fibrillations in the heart are distinguished in such a way that the heart returns to its normal sinus rhythm. With minimal experimentation, one of ordinary skill in the art will be able to determine the most advantageous stimulation using the cardiac wavefront controller with a linear array of electrodes in multiple locations. This would also be the case when the cardiac wavefront controller includes a surface of two dimensional array wrapped over the heart. Minimal experimentation will provide the ideal algorithm. Multiple, alternative algorithms might be useful to optimize treatment for a given patient, or group of patients.

A cardiac wavefront controller patch can be placed over the right atrium. This positioning provides control of the electrical properties of the entire right atrial surface, or a significant portion of the right atrial surface. A cardiac wavefront controller patch so installed can force the right atrium into a single electrical state. It can also be employed to forcing the initiation of a coordinated pattern of electrical activity towards the focal point from which the rest of the heart is paced.

Typically, a clinician would be using the cardiac wavefront controller patch to sense a fibrillation or a tachycardia. Electrodes in the cardiac wavefront controller patch or other electrodes can be employed to determine the nature of the diseased cardiac state. This information is then employed to provide control in order to get the heart out of that state and into a sinus rhythm. Measuring the EKG as an adjunct to the information from the cardiac wavefront controller patch is helpful in this regard.

The cardiac wavefront controller can be employed to measure the electrical wavefront locally. Implantable electrodes on the heart provide this information on a continuous basis. The a cardiac wavefront controller patch is so configured and programmed to react to the electrical a natural electrical wave fronts of the atrium and then pace responding to that wave front.

Production of multiple wave fronts is possible. A cardiac wavefront controller patch allows the imaging technician to better image the cardiac dynamics. This improved information is employed to craft an optimal control strategy. Software programs recognizing patterns in those wave fronts can respond to a stimulation algorithm that is best suited to the wave fronts that it identifies.

Once clinically relevant patterns are identified, algorithms are employed which are the most suitable to a particular pattern type. Different algorithms are made available by having multiple algorithms prestored in memory. When a specific type is identified, the device accesses and employs the optimal script.

Figure 10:
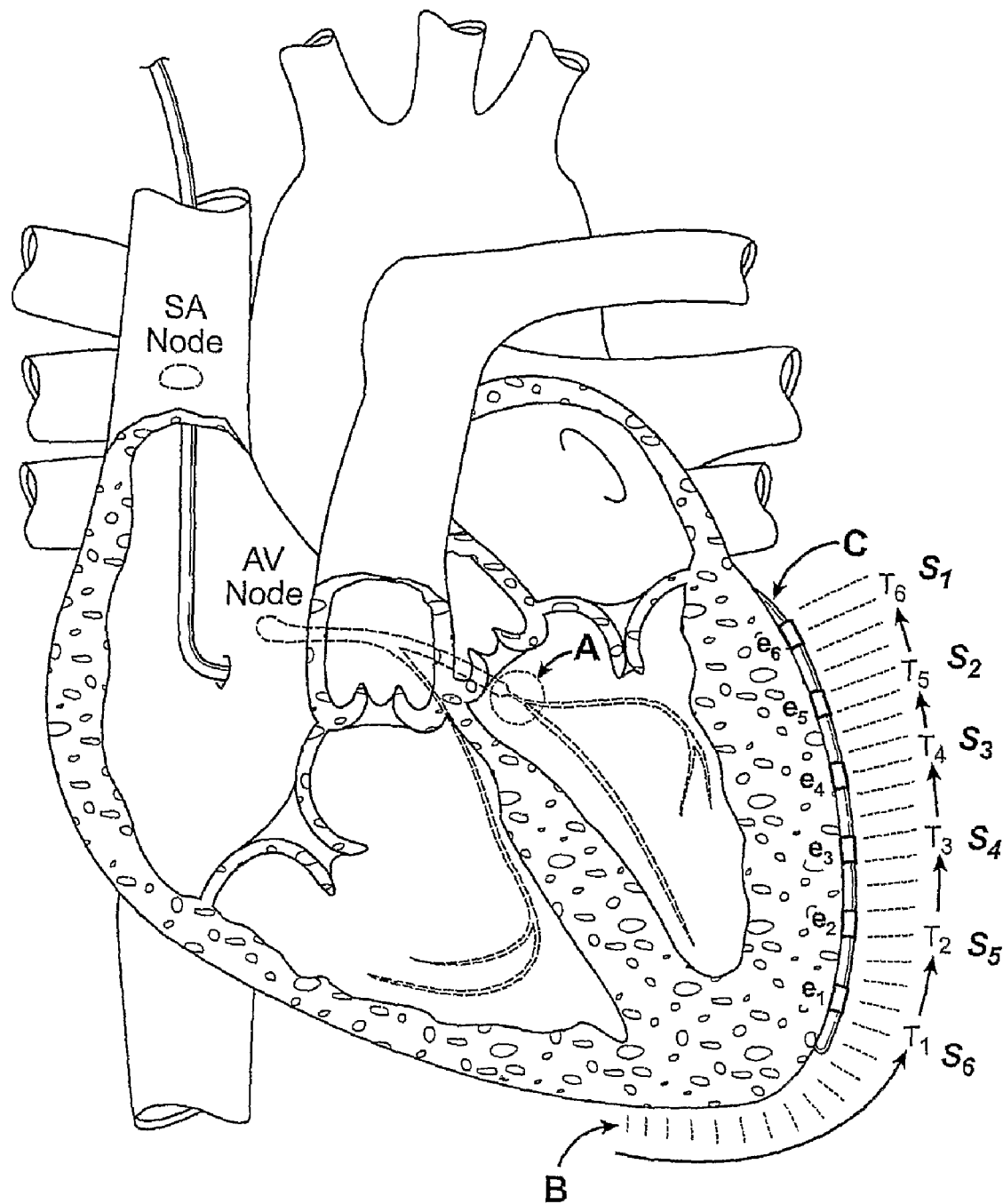
FIGS. 10-15 provide depictions of various embodiments of the cardiac wavefront controller aspect of the invention.

The cardiac wavefront controller is now further described in view of illustrative embodiments in conjunction with FIGS. 10 to 15. One anomaly in tissue conduction that may occur (and could be readily detected using the methods provided above) is a left bundle branch block. FIG. 10 shows a depolarization wave beginning at the SA node traveling out to the atria. It is then conducted through the AV node and through various bundles. As a result, the left and right ventricles contract simultaneously in a properly functioning heart.

A common pathology that creates dyssynchrony in heart failure is the called the left bundle branch block. In this case, the bundle going out to the left part of the heart is blocked. As a result, the depolarization wave moves down to the right ventricle, goes along the surface of the heart, and then up the left ventricle. The right ventricle contracts first and then the left ventricle contracts at a much later time. The block is shown as feature A. The resultant depolarization wave is shown by the wave fronts in feature B moving along the direction of the arrow.

The way one typically treats this in cardiac resynchronization therapy or biventricular pacing is a lead that is placed on the left side of the heart. A stimulus is applied at feature C. This causes the left ventricle which is timed such that the left ventricle contracts at the same time as the right ventricle.

A typical strategy that is used with single electrode leads is stimulation at the last activation. This means that stimulation is proved at the site that contracts last. It is looking at mechanical measures of dyssynchrony. By applying the electrical stimulus there a contraction is initiated, partially canceling out the effect of the delay by having the bundle branch block.

With the cardiac wavefront controller, a number of electrodes along a lead are provided. This is particularly effective with some of the present inventors quadrant pacing technology, e.g., as described in PCT application serial nos. PCT/US2005/031559 and PCT/US2005/046811; the disclosures of which are herein incorporated by reference. These features of this embodiment of the cardiac wavefront controller allow the device to apply very localized stimulus to the heart tissue.

Furthermore, using the cardiac wavefront controller, the depolarization wave feature B can be sensed as it moves past the various electrodes on the multi-electrode lead. In this case, the cardiac wavefront controller allows quantification of the natural contractile pattern of the heart. Using this information, a series of pulses are applied to counteract the natural contractile pattern, returning the heart to a healthy synchronous rhythm.

By example, if the depolarization wave were detected by the cardiac wavefront controller to be moving up at time 1 on electrode 1, time 2 on electrode 2, and time 3 on electrode 3, feedback is provided. The cardiac wavefront controller can then optimally stimulate the electrodes in succession. This causes a depolarization wave to move back in the other direction.

In that case, stimulation can be provided in a reverse sense, such as S1, S2, S3, S4, S5, S6 and in this way the exact timing of the contraction of the various segments of the heart can be controlled. In the event of a left bundle branch block, this is how the cardiac wavefront controller can be employed.

Another pathology that occurs is when there are other types of blocks on the surface of the heart. The next type of abnormality is a more general block. By example, somewhere on the surface of the heart there is some scar tissue. That can also block the depolarization wave.

Figure 11:
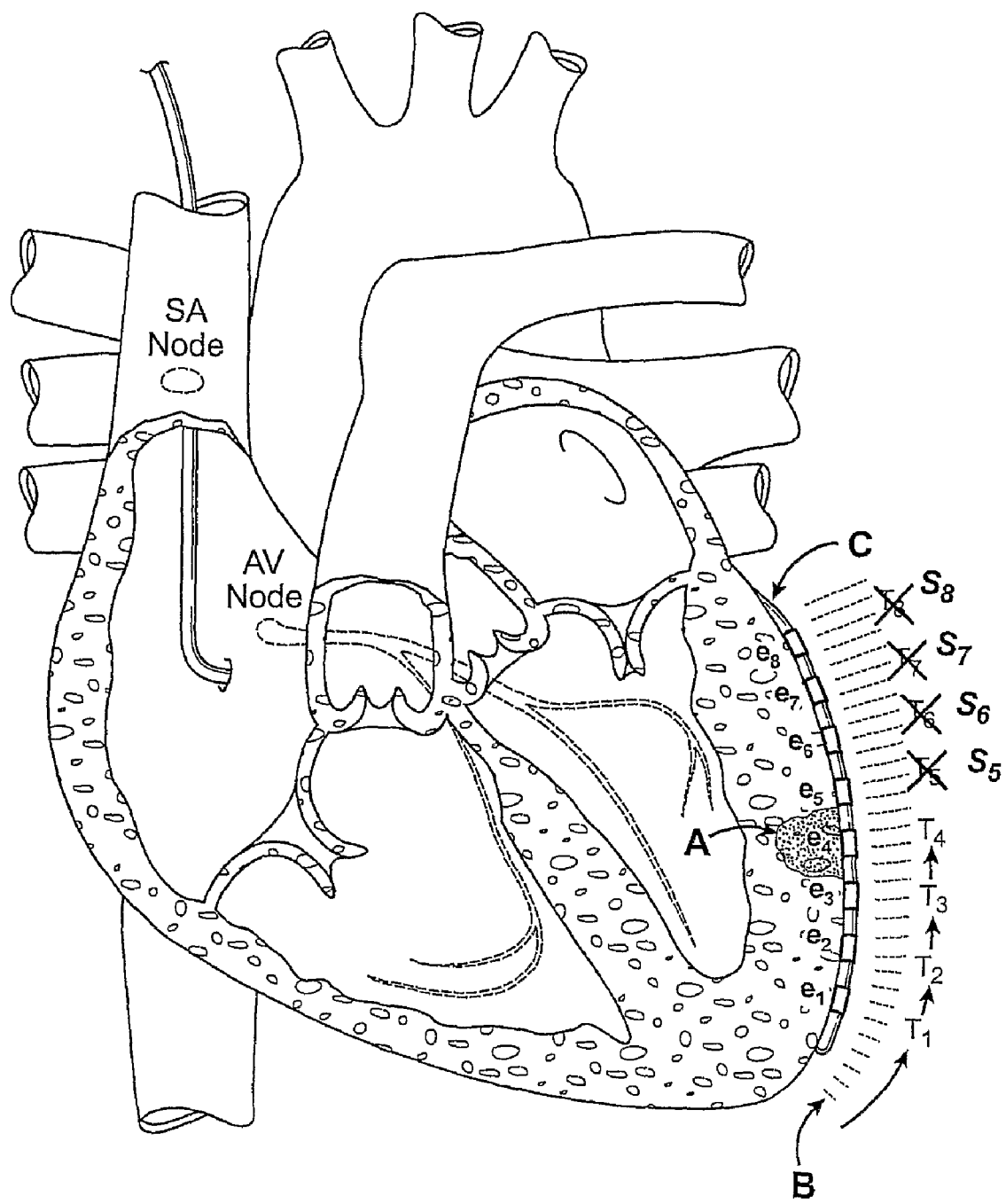

In FIG. 11, feature A is scar tissue. Again, the depolarization wave is coming up from the apex of the heart feature B and becomes blocked at feature A. As a result, all the tissue higher up the heart above feature A does not contract. On installation of a cardiac wavefront controller on a lead as illustrated, the device initiates contraction at feature C causing more of the heart to contract.

The cardiac wavefront controller may be employed to localize exactly where the block or other region of abnormal conduction is present. This is done by observing the depolarization wave moving through T1, T2, T3, T4, and then noting that it stops. No depolarization wave would be observed at T5 and at T6 and so forth. This allows determination of exactly which electrodes should be stimulated.

Furthermore, the stimulation can be tailored exactly to the propagation of the conduction waves. By measuring the times at which depolarization passes the T1, T2, T3, T4 points, one can extrapolate and stimulate at the post block sites S5, S6, S7, and S8 with a stimulation time that is an exact extrapolation of the contractile time at the T1-T4. In this way even though there is a block, the normal depolarization wave motion to the heart is restored.

Figure 12:
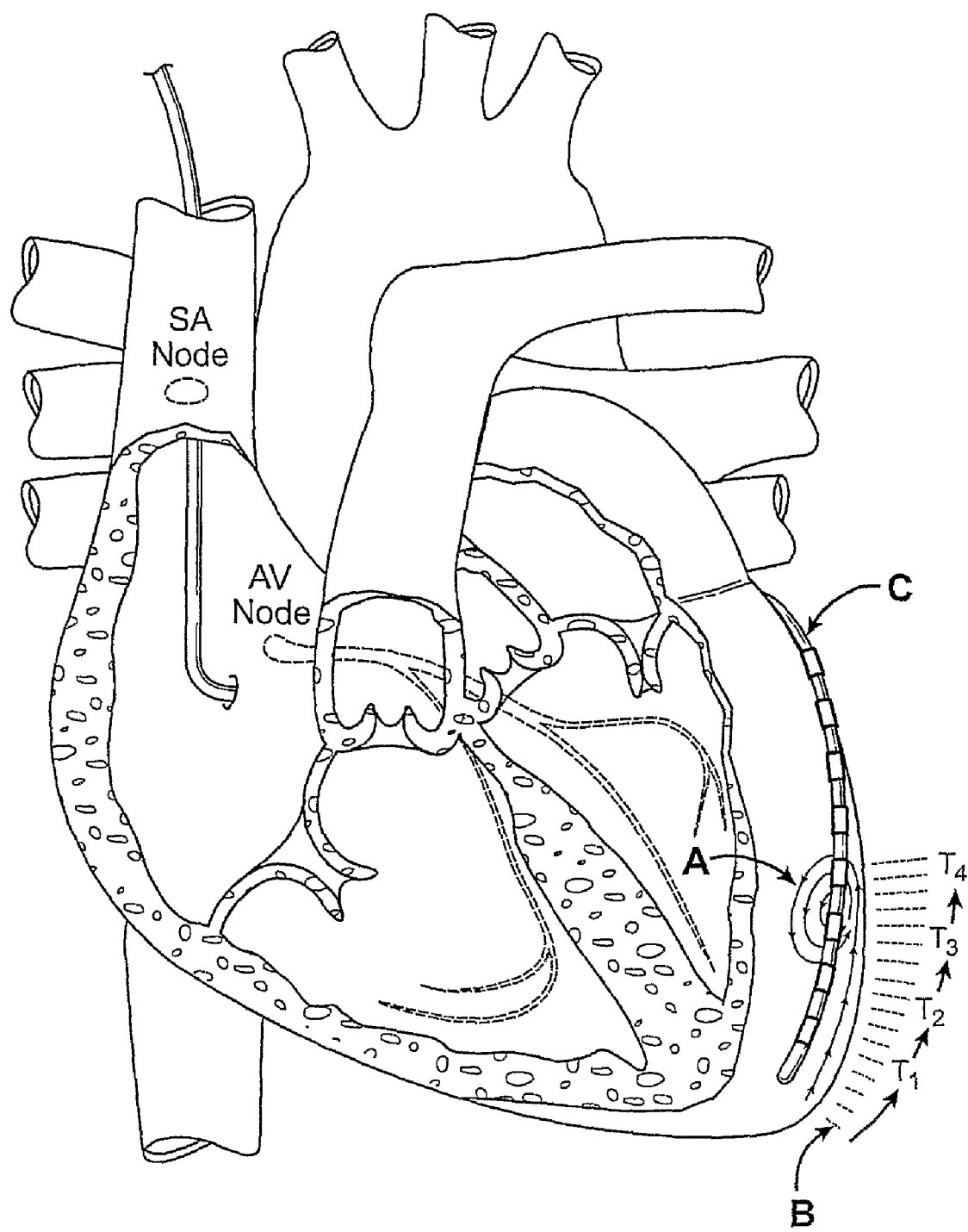

FIG. 12 illustrates a different type of abnormality which is a reentrant circuit. An example is as described above regarding atrial flutter. It is also possible to get ventricular defibrillation. The nature of this can occur anywhere in the heart, although it is illustrated here on the left side. On the surface of the heart, instead of the depolarization wave moving linearly, for whatever reason it moves in a type of circular fashion. This is illustrated schematically as feature A. As a result, the heart, instead of being tied to the initiation at the SA node, shows little local features that can stimulate themselves. This phenomena results in flutters and fibrillations. The effected part of the heart beats repeatedly without any external stimulus and it is very wasteful.

A common way to address these pathologies is through ablation treatment. In this case, the treatment is to essentially burn out a little section of heart tissue to block this reentrant circuit. The cardiac wavefront controller provides a more dynamic way of treating these pathologies. The cardiac wavefront controller multi-electrode lead embodiment can come down over the surface of the heart. The first step is to map out these reentrant circuits to determine, in this case, a T3 and T4 abnormality. These show repeatedly the depolarization wave going over those points as this reentrant circuit runs around in a circle.

Treatment is accomplished by applying pulses with precise timing. By example, T3, T4 are observed going on and off repeatedly. A pulse is applied during the refractory period right after or before T3 would normally fire. The refractory period is induced in such a timing so that when the reentrant circuit in the depolarization wave comes to T3 the heart muscles are in a refractory period. As a result, the tissues and do not respond to the wavefront. The circuit is effectively broken, shutting down the reentrant nature of the pathology. This treatment can be performed every cardiac cycle to in effect turn off the reentrant circuit on each pulse.

Figure 13A:
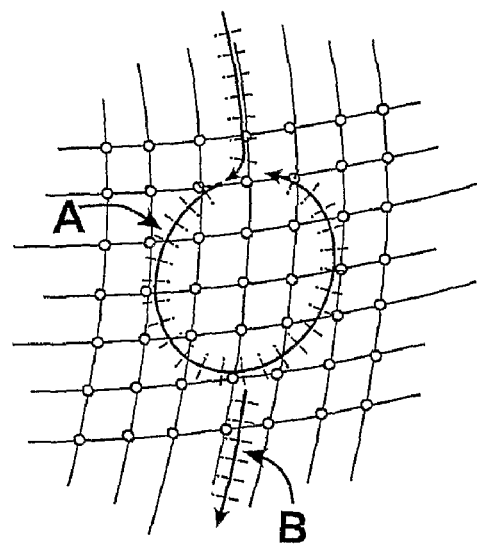
Figure 13B:
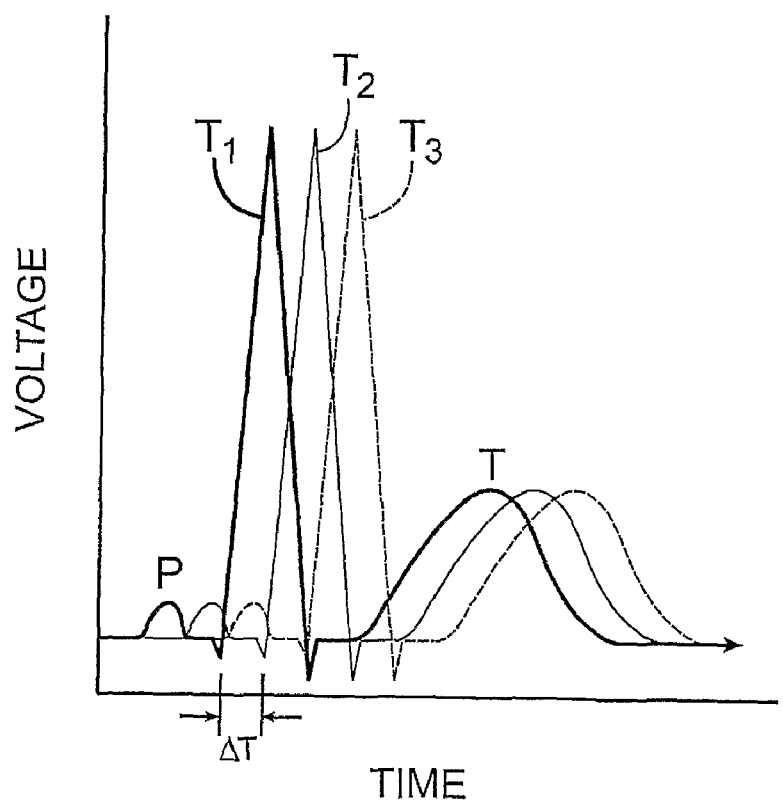

There is also much that can be accomplished by the cardiac wavefront controller in this way in a two dimensional fashion. Typically these circuits are on the surface of the heart and they are circular in nature. With a cardiac wavefront controller in a two dimensional array of electrodes, a sock could be integrated (in some cases with a constraint device) which allows mapping out in two dimensions of the nature of reentrant circuit, as shown in FIG. 13A. of interest in certain embodiments is the use of a deployable epicardial device as described in PCT application serial no. PCT/US2006/0245648; the disclosure of which is herein incorporated by reference.

FIG. 13A shows the mesh. At the vortexes of this mesh there are sensing and stimulation capability. A reentrant circuit can occur where when the depolarization wave comes down it hits some point. Instead of going straight, it forms kind of a circular trajectory. When the depolarization wave first comes it appears as the area above A. However, when it gets to A, it goes circular.

With the two dimensional mesh embodiment of cardiac wavefront, there is the capacity to map out the nature of that reentrant circuit very precisely. Once the dynamics of the anomaly are detected, it is stimulated so as to put the appropriate portions of the muscle into a refractory period to intercept the reentrant circuit and block it.

One other thing that happens is that the depolarization wave gets caught in the reentrant circuit. In this case, the cardiac wavefront controller applies stimulation afterwards at the appropriate time at point B. This treatment reinitializes the depolarization wave at point B so that it continues down to the rest of the heart instead of getting blocked up in the reentrant circuit feature A. This two dimensional technique of the cardiac wavefront controller also translates over to the other two abnormalities disused above. With more stimulations points, there are more spatial sensing points that can characterize the depolarization wave more directly and the spatial characterizations of it by sensing voltages and then apply precise stimuli to recreate the desired wave form.

Techniques are well established for sensing voltages. One can take an internal cardio-electrogram on each electrode of the cardiac wavefront controller with a common time base. This can be done in a multiplex cache with the multi-electrode lead. Sampling the voltage on each electrode in succession is done to observe the initiation of the QRS sequence. This is shown diagrammatically in FIG. 13B. It shows a dashed arrow at the initiation of the QRS sequence indicating the passage of the depolarization wave.

At different points such as T1 and T2 one can observe something slightly delayed. The time difference between the two Q points ΔT is measured. The depolarization wave velocity is characterized where the velocity is simply the distance between T1 and T2. These last features are known because of the construction of the multi-electrode lead divided by ΔT.

This sensing/analysis/firing process of the cardiac wavefront controller can be accomplished successively for all the electrodes. By example, for the third electrode another slightly shifted wave would be observed, as illustrated by the dashed line T3. Then at T4 if there were a block, no depolarization wave would be observer. This would indicate a block at that point.

The cardiac wavefront controller would then be employed to apply stimulation exactly at the timing determined by the velocity. When the velocity is known, and there is a block at T4, the cardiac wavefront controller would optimally stimulate at a time T=velocity*distance between T1 and T4. This is a simple linear extrapolation.

The effect would be analoguous to providing a jumper for the depolarization wave over the block at T4. A similar expression would be provided for the other Ts; by example, if time is stimulated at Ti where conduction velocity * the distance between the first electrode and the ith electrode. The cardiac wavefront controller would be used to apply multiple stimuli at multiple electrodes at multiple times to precisely create the desired depolarization wave.

In this way even in a heart with very limited electrical conductivity one can obtain effective treatment by the cardiac wavefront controller. Consider a very diseased heart in which there are only little patches of cell which have some contractility and responsivity. However, for the most part these are disconnected and do not communicate with each other. By use of the cardiac wavefront controller, an artificial electrical conduction system is created in this manner. The therapy causes these small patches of muscle which are completely useless in a very diseased heart to be brought back into use, and create a marginal increase in cardiac output. As such, the cardiac wavefront controller can be employed in people with very severe heart attacks to bring more muscle back into play and bring more strength to their heart.

Figure 14:
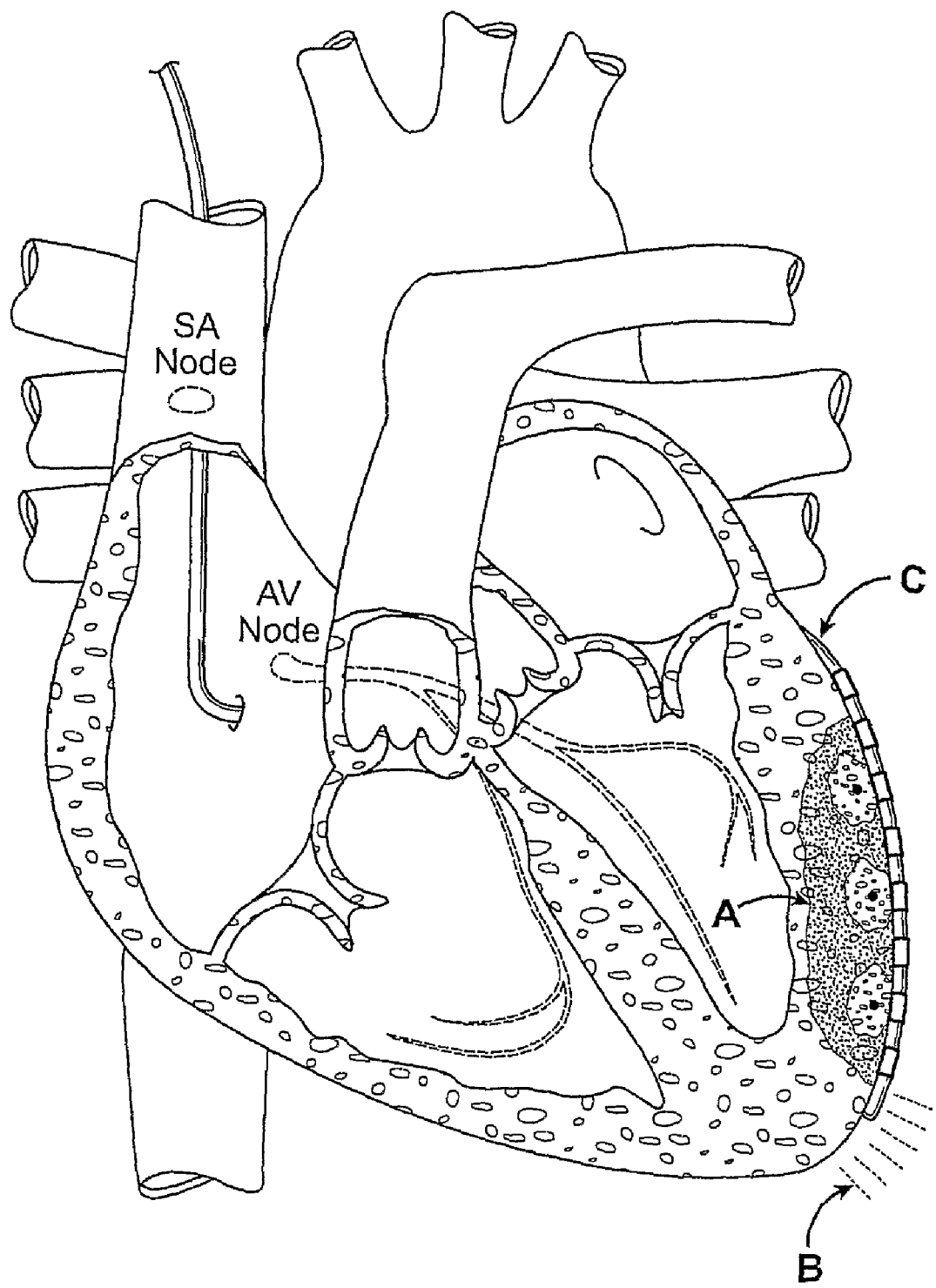

As medicine moves towards biologics where stem cells are employed to re-grow parts of the heart, the cardiac wavefront controller can be employed as a means to rewire the new patches of cardiac muscle into the rest of the conduction system in the rest of the heart. In FIG. 14 some diseased heart with some healthy tissue below is illustrated. In FIG. 14 there is some healthy tissue in feature A and at Feature B. Some stem cells are planted which grow out to produce new heart tissue around them.

The depolarization wave will move through feature A and then it will stop. More stem cells are planted and each of these grow around some region. However, a disconnected series of patches results, as illustrated.

With the multi-electrode lead cardiac wavefront controller, several electrodes along the length of the device are used to connect the depolarization wave from B. They stimulate at exactly the right time in all of these multi-electrodes to cause the different patches to contract at the right time. This treatment brings the whole heart back together despite the absence of natural electrical conductive system. The new muscle inserted because of disease has been provided as an artificial electrical conduction system. This allows parts of muscle to be utilized in the pumping function which would otherwise not be used back into play in the heart.

Referring to U.S. Pat. No. 6,663,622, the conductance between two points is used to determine the viability of cardiac tissue. In this case it is in the context of ablation, but that same approach can be applied in a different context. In an infarcted heart, there are patches of live tissue and patches of dead tissue. The clinician wants to determine where the dead tissue is. With the cardiac wavefront controller multi-electrode lead, the regions of impaired conductivity can be identified.

Figure 15:
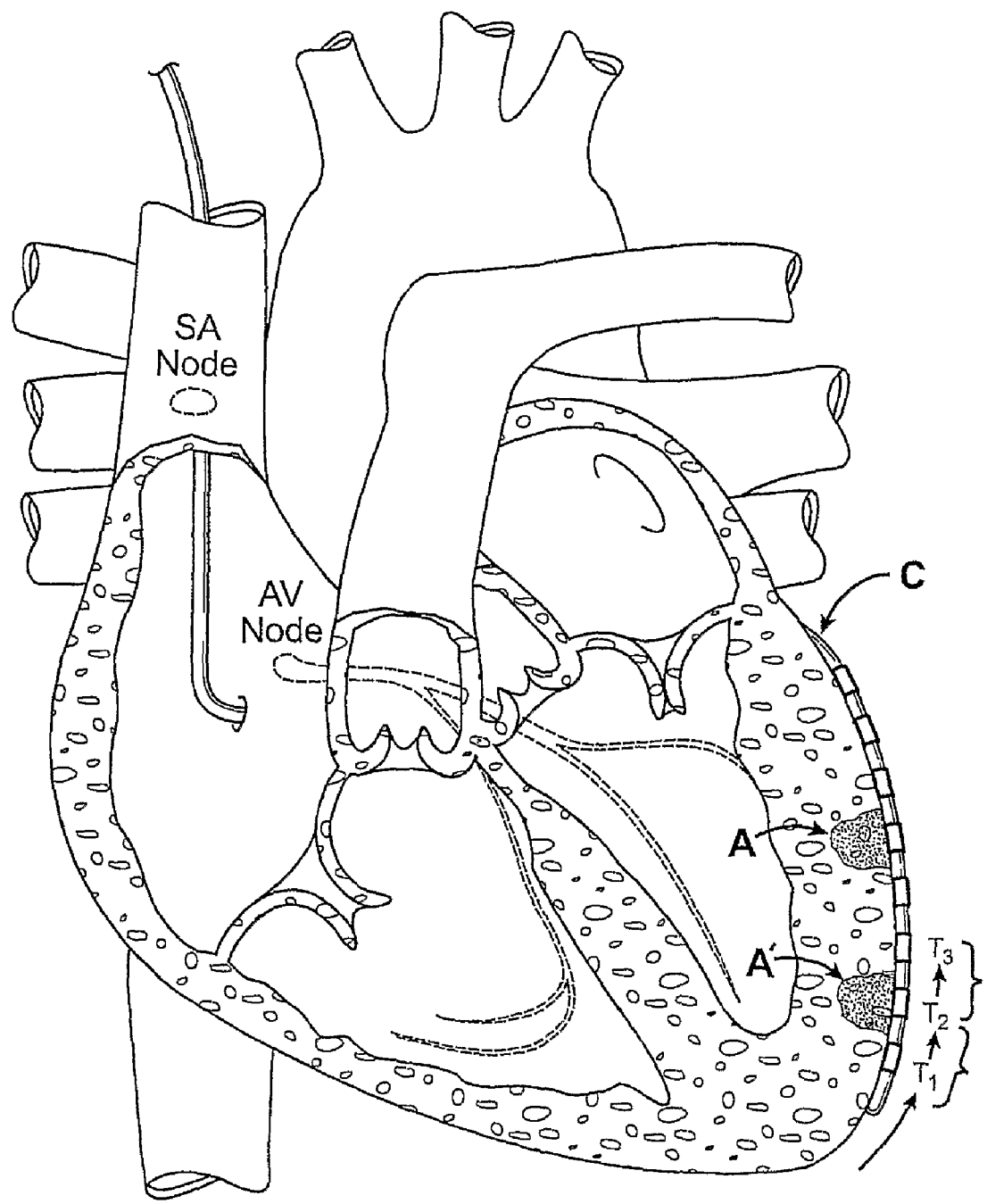

In FIG. 15 is illustrated a multi-electrode lead along the side with many electrodes shown as circles. An infarcted portion is shown at feature A, which is dead tissue and then healthy tissue. Another infarcted portion is at feature A'.

In this application of the cardiac wavefront controller the parallelized conductivity between the electrodes on the leads is measured between T1 and T2. A very different number is given between the healthy tissue if the measurement is taken between T2 and T3. In this way one could build up a profile of the viability of different segments of tissue along the heart. One could then determine exactly which portions of the cardiac tissue are viable and which are not viable. Stimulus is then appropriately applied to "jump over" or cause the depolarization wave to jump over the parts that are not viable. This can be accomplished from originally viable points, where stimuli of varying intensity is applied to bring them back into viability. In this way, when a patchwork of viable and nonviable tissue is available, one can use the cardiac wavefront controller in its multi-electrode lead embodiment to first sense where the problems are and then stimulate to rewire the natural electrical conductive system around those blockages is advantageous.

Another way to sense this that is not electrophysiological is as follows. A special protein dye is employed on cardiac tissue grown on a plate. The dye fluoresces when the depolarization wave passes by. One could decouple sensing from the stimulus. One could inject this dye causing this fluorescent pattern. Photodetectors are then integrated in with the multi-electrode lead to see exactly when different portions of the heart fluoresce providing information as to when the depolarization wave is going by. That information is recorded. In more of an open loop fashion, the cardiac wavefront controller stimulates according to that data.

Another way to sense regions of impaired conductivity is to employ a wave length of light in the red where the body is transparent. One could tailor this dye so the fluorescence fluoresces in the window where the body is transparent. By simply facing the camera outside of the body, one could record the depolarization wave in a very visual fashion. One would then map out the two-dimensional nature with very high resolution and correlate that back and adjust stimulus appropriately to optimize. In this way, one would be able to see the reentrant circuits very clearly.

The reentrant circuits are visualized by little spirals that would form. One could visualize those directly in living heart tissue and then one could program a multi-electrode lead as desired, either pre or post-implantation. This information can be used to determine where the best place to implant the lead might be, be it an epicardial lead or some kind of two dimensional sock type array or multi-electrode lead. These techniques provide the optimum strategy for placing the lead based on the electrophysiology as it really exists in a patient's heart.

Where employed, a camera can be directly integrated in with the fluoroscopy system overlay so one could have an overlay image of the fluoroscopy image showing the contraction of the heart with the fluorescence recorded by a co-located camera directly on top of the image. Using data fusion techniques, one could see both the mechanical and electrical contractile properties of the heart simultaneously and then optimize placement appropriately.

The cardiac wavefront controller enjoys many advantages over currently available defibrillation devices. The cardiac wavefront controller can be employed as an adjunct to currently available devices. It also has the advantage of treating pre-clinical wavefront problems.

The prevalence of fibrillation is high in cardiac patients. Both atrial and ventricular arrhythmias are also prevalent. The cardiac wavefront controller can be employed effectively for both atrial and ventricular defibrillations as well as arrhythmias. The cardiac wavefront controller consumes up far less energy than present systems. The big shock currently administered will drain a battery. It is also very painful to the patient, as 20 or 30 joules are being released simultaneously. Some patients have compared this therapy to the feeling of being kicked by a horse.

By contrast, in the case of the cardiac wavefront controller treatment, in many cases the patient would not feel it, and not be aware that treatment has been administered. If anything, the patient will feel a sensation similar to a tickle or a sense like a regular pacing pulse. Such pulses are generally not felt by the patient. However, the patient might feel the normal symptoms of arrhythmia or fibrillation which is not so comfortable The cardiac wavefront controller therapy would be much friendlier to the patient and would allow the batteries to last much longer.

Today fibrillation devices are replacing every 3 to 5 years depending on how often they are fired and this device could have a 10-15 year life span. Because of the low sensation of treatment, it may be advantageous for the device to report treatment back to the physician or patient that an event occurred.

The cardiac wavefront controller has advantages over current atrial fibrillations treatment. These fibrillation may occur all the time. They are treated with medications that are minimally effective, with the complication that they may lead to the more serious ventricular fibrillation. Atrial fibrillation might lead to heart failure and a not highly efficient heart. The cardiac wavefront controller provides a simple means of resynchronizing the atrium at a local level, making the atrium is more efficient.

In certain embodiments, the cardiac wavefront controller communicates to a central communication node which then sends data to the outside body. Such communication may be integrated with a variety of different sensors, such as oxygen sensors, hematocrit sensors, viscosity sensors, accelerometers and the like, providing a more complete clinical profile of the patient's cardiac state. Pressure sensors such as those developed by some of the present inventors (see e.g., U.S. Pat. Nos. 7,013,734; 7,007,551; and 7,028,550; as well as application Ser. Nos. 11/025,366, 11/025,795 and 11/025,793; the disclosures of which are herein incorporated by reference) are particularly suitable. These and other sensing modalities may be employed to influence the algorithm selection to pull the heart out of fibrillation a low pressure state. These are often different than a relatively high pressure state. A low oxygen content on the right side might be dealt with differently as well.

Other useful iterative data includes sensors showing if the wounds are full of fluid by measuring impedance. A different electrical algorithm in that case may be selected. In any fibrillation event, one could a sync up with all these sensing modalities and record all of that information simultaneously. The treating physician would then be provided a more complete picture of what actually is going on during the fibrillation event or flutter event, and have clues in terms of how to treat it This data can also be allied to detection of pill ingestions. If the patient ingests a pill and with in a certain period of time fibrillation event occurs, a record can be provided as to how many fibrillation events occurred since taking the pill. This can establish the level of effectiveness of the pill or the pharmacological agent and the stimulation protocol. This information allows identification of stimulation protocols which are more efficient in the presence of certain pharmaceutical agents.

Utility

The systems and methodologies in accordance with the invention find use in a variety of different applications. The systems and methodologies of the invention are useful in determining depolarization wave conduction velocities through a variety of different tissues, including cardiac tissue. The systems and methodologies may be employed with a variety of different kinds of animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the subjects or patients will be humans.

As reviewed above, the subject methods may be employed to determine conduction velocities of depolarization waves through cardiac tissues in one dimension, two dimensions and even three dimensions. As multi-dimensional velocity data can be readily obtained with the present systems and methods, additional information regarding directionality of wave propagation can also be obtained. Furthermore, regions or areas of abnormal wave conduction can be readily identified, i.e., mapped.

As such, applications in which the present invention finds use include diagnostic applications, where the systems and methods are employed in the identification of regions of abnormal conductivity and, accordingly, the diagnosis disease conditions or even pre-disease conditions. In this manner one can monitor a patient for the development of abnormal conductivity regions and intervene at an early stage before serious complications manifest.

The systems and methods may be readily employed as an ischemia detector. As reviewed above, the systems and methods may be employed to readily identify regions of abnormal conductivity, including no conductivity, and attribute this lack of conductivity to ischemia. In addition, the methods and systems may readily be employed to identify pre-ischemic regions, which may appear only when the tissue is stimulated in some manner, e.g., by medicine, exercise and the like. Another application of technology is as a superior arrhythmia detection circuit. Additional applications in which the subject invention finds use include, but are not limited to: the detection of electromechanical dissociation during pacing or arrhythmias, differentiation of hemodynamically significant and insignificant ventricular tachycardias, monitoring of cardiac output, mechanical confirmation of capture or loss of capture for autocapture algorithms, optimization of multi-site pacing for heart failure, rate responsive pacing based on myocardial contractility, detection of syncope, detection or classification of atrial and ventricular tachyarrhythmias, automatic adjustment of sense amplifier sensitivity based on detection of mechanical events, determination of pacemaker mode switching, determining the need for fast and aggressive versus slower and less aggressive anti-tachyarrhythmia therapies, or determining the need to compensate for a weakly beating heart after therapy delivery (where these representative applications are reviewed in greater detail in U.S. Pat. No. 6,795,732, the disclosure of which is herein incorporated by reference), and the like.

In certain embodiments, the subject invention is employed to overcome barriers to advances in the pharmacologic management of CHF, which advances are slowed by the inability to physiologically stratify patients and individually evaluate response to variations in therapy. It is widely accepted that optimal medical therapy for CHF involves the simultaneous administration of several pharmacologic agents. Progress in adding new agents or adjusting the relative doses of existing agents is slowed by the need to rely solely on time-consuming and expensive long-term morbidity and mortality trials. In addition, the presumed homogeneity of clinical trial patient populations may often be erroneous since patients in similar symptomatic categories are often assumed to be physiologically similar. It is desirable to provide implantable systems designed to capture important cardiac performance and patient compliance data so that acute effects of medication regimen variation may be accurately quantified. This may lead to surrogate endpoints valuable in designing improved drug treatment regimens for eventual testing in longer-term randomized morbidity and mortality studies. In addition, quantitative hemodynamic analysis may permit better segregation of drug responders from non-responders thereby allowing therapies with promising effects to be detected, appropriately evaluated and eventually approved for marketing. The present invention allows for the above. In certain embodiments, the present invention is used in conjunction with the Pharma-informatics system, as described in PCT Application Serial No.: PCT/US2006/016370; the disclosures of which are herein incorporated by reference.

The methods and systems may also find use in conjunction with determination of appropriate therapies, and even implementation thereof, e.g., as described above. For example, following detection of abnormal conductivity regions, the systems may be employed in a cardiac wavefront controller format (as reviewed above) to treat the subject for the abnormal conductivity region.

Computer Readable Medium

One or more aspects of the subject invention may be in the form of computer readable media having programming stored thereon for implementing the subject methods. The computer readable media may be, for example, in the form of a computer disk or CD, a floppy disc, a magnetic "hard card", a server, or any other computer readable media capable of containing data or the like, stored electronically, magnetically, optically or by other means. Accordingly, stored programming embodying steps for carrying-out the subject methods may be transferred or communicated to a processor, e.g., by using a computer network, server, or other interface connection, e.g., the Internet, or other relay means.

More specifically, computer readable medium may include stored programming embodying an algorithm for carrying out the subject methods. Accordingly, such a stored algorithm is configured to, or is otherwise capable of, practicing the subject methods, e.g., by operating an implantable medical device to perform the subject methods. The subject algorithm and associated processor may also be capable of implementing the appropriate adjustment(s).

Of particular interest in certain embodiments are systems loaded with such computer readable mediums such that the systems are configured to practice the subject methods.

Systems

Aspects of the invention include systems, including implantable medical devices and systems, which include the devices of the invention. The systems may perform a number of different functions, including but not limited to diagnostic applications, electrical stimulation applications, e.g., for medical purposes, such as pacing, etc.

The systems may have a number of different components or elements in addition to the one or more sets of satellites, where such elements may include, but are not limited to: sensors (e.g., cardiac wall movement sensors, such as wall movement timing sensors); processing elements, e.g., for controlling timing of cardiac stimulation, e.g., in response to a signal from one or more sensors; telemetric transmitters, e.g., for telemetrically exchanging information between the implantable medical device and a location outside the body; drug delivery elements, etc. As such, the subject systems may include one or more sets of satellites that are operably coupled, e.g., in electrical communication with, components of a number of different types of implantable medical systems, where such systems include, but are not limited to: physiological parameter sensing devices; electrical (e.g., cardiac) stimulation devices, etc.

In certain embodiments of the subject systems, one or more sets of satellites as described above are electrically coupled to at least one elongated conductive member, e.g., an elongated conductive member present in a lead, such as a cardiovascular lead. In certain embodiments, the elongated conductive member is part of a multiplex lead, e.g., as described in Published PCT Application No. WO 2004/052182 and U.S. patent application Ser. No. 10/734,490, the disclosure of which is herein incorporated by reference. In some embodiments of the invention, the devices and systems may include onboard logic circuitry or a processor, e.g., present in a central control unit, such as a pacemaker can. In these embodiments, the central control unit may be electrically coupled to one or more deployable arrays via one or more conductive members.

In certain embodiments, the implantable medical systems which include the subject satellite sets are ones that are employed for cardiovascular applications, e.g., pacing applications, cardiac resynchronization therapy applications, etc.

Embodiments of the subjects systems incorporate one or more effector elements. The effectors may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. As such, the effectors may be sensors, e.g., temperature sensors, accelerometers, ultrasound transmitters or receivers, voltage sensors, potential sensors, current sensors, etc. Alternatively, the effectors may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like.

Effectors of interest include, but are not limited to, those effectors described in the following applications by at least some of the inventors of the present application: U.S. patent application Ser. No. 10/734,490 published as 20040193021 titled: "Method And System For Monitoring And Treating Hemodynamic Parameters"; U.S. patent application Ser. No. 11/219,305 published as 20060058588 titled: "Methods And Apparatus For Tissue Activation And Monitoring"; International Application No. PCT/US2005/046815 titled: "Implantable Addressable Segmented Electrodes"; U.S. patent application Ser. No. 11/324,196 titled "Implantable Accelerometer-Based Cardiac Wall Position Detector"; U.S. patent application Ser. No. 10/764,429, entitled "Method and Apparatus for Enhancing Cardiac Pacing," U.S. patent application Ser. No. 10/764,127, entitled "Methods and Systems for Measuring Cardiac Parameters," U.S. patent application Ser. No. 10/764,125, entitled "Method and System for Remote Hemodynamic Monitoring"; International Application No. PCT/US2005/046815 titled: "Implantable Hermetically Sealed Structures"; U.S. application Ser. No. 11/368,259 titled: "Fiberoptic Tissue Motion Sensor"; International Application No. PCT/US2004/041430 titled: "Implantable Pressure Sensors"; U.S. patent application Ser. No. 11/249,152 entitled "Implantable Doppler Tomography System," and claiming priority to: U.S. Provisional Patent Application No. 60/617,618; International Application Serial No. PCT/USUS05/39535 titled "Cardiac Motion Characterization by Strain Gauge". These applications are incorporated in their entirety by reference herein.

Use of the systems may include visualization of data obtained with the devices. Some of the present inventors have developed a variety of display and software tools to coordinate multiple sources of sensor information which will be gathered by use of the inventive systems. Examples of these can be seen in international PCT application serial no. PCT/US2006/012246; the disclosure of which application, as well as the priority applications thereof are incorporated in their entirety by reference herein.

Data obtained using the implantable embodiments in accordance with the invention, as desired, can be recorded by an implantable computer. Such data can be periodically uploaded to computer systems and computer networks, including the Internet, for automated or manual analysis.

Uplink and downlink telemetry capabilities may be provided in a given implantable system to enable communication with either a remotely located external medical device or a more proximal medical device on the patient's body or another multi-chamber monitor/therapy delivery system in the patient's body. The stored physiologic data of the types described above as well as real-time generated physiologic data and non-physiologic data can be transmitted by uplink RF telemetry from the system to the external programmer or other remote medical device in response to a downlink telemetry transmitted interrogation command. The real-time physiologic data typically includes real time sampled signal levels, e.g., intracardiac electrocardiogram amplitude values, and sensor output signals including dimension signals developed in accordance with the invention. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/therapy delivery system thus develops a variety of such real-time or stored, physiologic or non-physiologic, data, and such developed data is collectively referred to herein as "patient data".

Kits

As summarized above, also provided are kits for use in practicing the subject methods. Embodiments of the kits include a computer readable medium, as described above. The computer readable medium may be a component of other devices or systems, or components thereof, in the kit, such as an adaptor module, a pacemaker, etc. The kits and systems may also include a number of optional components of the various systems, such as multiplex leads, central controllers, etc.

In certain embodiments of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

The following examples are offered by way of illustration and not by way of limitation.

EXPERIMENTAL

I. Evaluation of the Effect of Lidocaine on Conduction Velocity

Figure 16A:
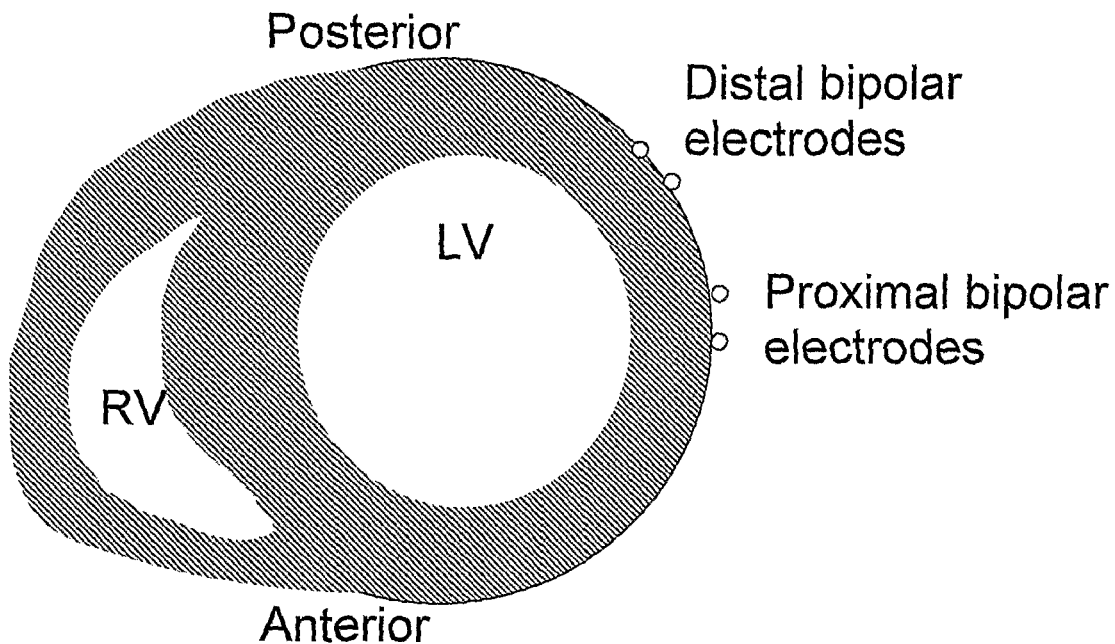
FIGS. 16A-16B provide depictions of information described in the experimental section, below.
Figure 16B:
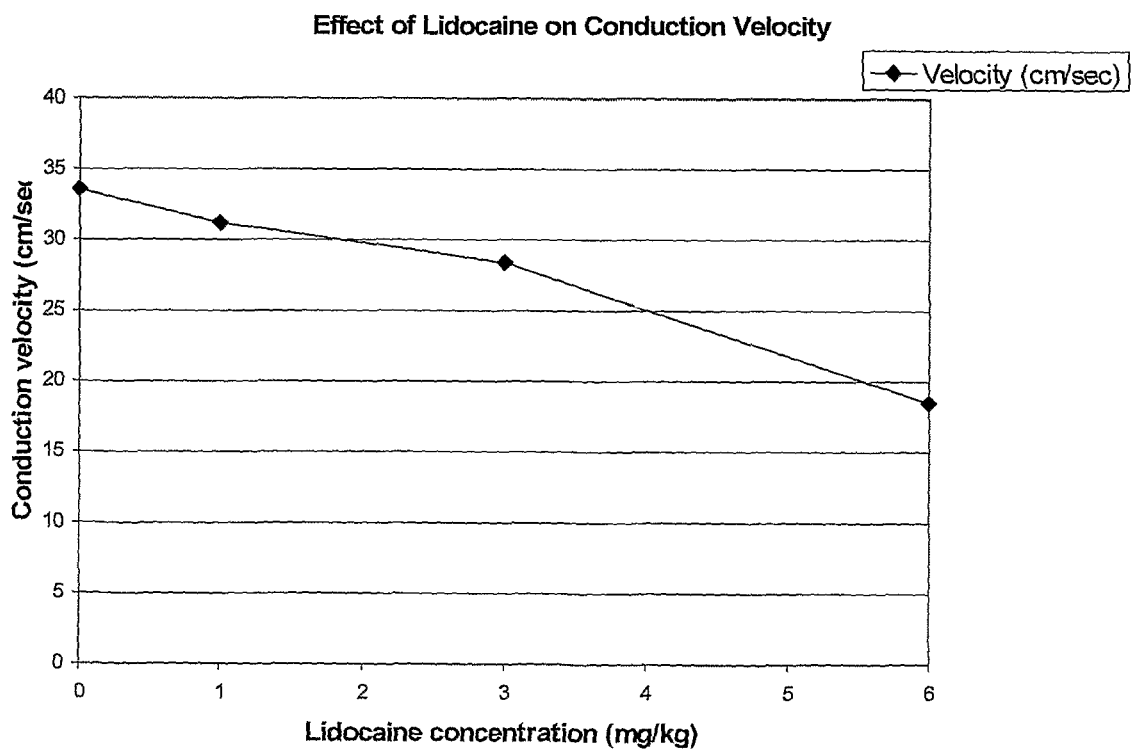

Change in conduction velocity after injection of lidocaine using EP catheter placed in cardiac vein of LV is measured as follows. A pair of bipolar electrodes is positioned on the epicardial surface of the left ventricle as shown in FIG. 16A. Various concentrations of lidocaine are administered and the conduction velocity is determined for each dosage, in accordance with the methods of the invention. The results are graphically depicted in FIG. 16. B.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of determining conduction velocity of a depolarization wave in a tissue, the method comprising:
    (a) providing a first satellite coupled to a central controller, the first satellite having a first satellite circuit and at least two individually and separately addressable first satellite electrodes, the first satellite circuit adapted to simultaneously and separately couple and decouple each of the at least two first satellite electrodes as directed by the central controller;
    (b) providing a second satellite coupled to the central controller, the second satellite having a second satellite circuit and at least two individually and separately addressable second satellite electrodes, the second satellite circuit adapted to simultaneously and separately couple and decouple each of the at least two second satellite electrodes as directed by the central controller;
    (c) determining a time interval between a first satellite's reporting of a depolarization wave in the tissue and a second satellite's reporting of a depolarization wave in the tissue, wherein the first satellite and the second satellite are formed on a lead, and wherein the second satellite is located a fixed distance away from the first satellite; and
    (d) calculating the conduction velocity using the time interval and the fixed distance between the first satellite and the second satellite.

2. The method according to claim 1, wherein the first and second satellites are coupled to at least one conductive element within the lead.

3. The method according to claim 2, wherein the lead comprises two wires and the first and second satellites are each coupled to the two wires.

4. The method according to claim 2, wherein the lead comprises a single wire and the first and second satellites are each coupled to the single wire.

5. The method according to claim 2, wherein the at least one conductive element is coupled to the central controller.

6. The method according to claim 1, wherein each of the first and second satellites comprises a circuit and at least one effector coupled to the circuit.

7. The method according to claim 5, wherein the method further comprises configuring the first and second satellites to report a presence of the depolarization wave to the central controller.

8. The method according to claim 7, wherein the configuring the first and second satellites are performed sequentially.

9. The method according to claim 7, wherein each of the first and second satellites comprises an effector, and wherein the method further comprises coupling the effector to the at least one conductive element.

10. The method according to claim 9, wherein the coupling of the first and second satellites is performed sequentially.

11. The method according to claim 1, wherein the method further comprises applying a stimulus to the tissue to produce the depolarization wave.

12. The method according to claim 11, wherein the stimulus is a pharmacological stimulus.

13. The method according to claim 12, wherein the pharmacological stimulus is applied by administering a medication.

14. The method according to claim 11, wherein the stimulus is an electrical stimulus.

15. The method according to claim 14, wherein the electrical stimulus is applied by causing the first satellite to depolarize the tissue.

16. The method according to claim 11, wherein the stimulus is a physical stimulus.

17. The method according to claim 16, wherein the physical stimulus is applied when a host that comprises the tissue is exercising.

18. The method according to claim 1, wherein the tissue is a cardiac tissue.

19. The method according to claim 1, wherein the method further comprises obtaining a second conduction velocity from a third and fourth satellites, wherein the third and fourth satellites are positioned at different locations of the tissue.

20. The method according to claim 19, wherein the third and fourth satellites are present on a second lead.

21. The method according to claim 19, wherein the method further comprises determining a direction of the depolarization wave in the tissue from the first conduction velocity and the second conduction velocity.

22. The method according to claim 21, wherein the method comprises evaluating conductive properties of a portion of the tissue using the determined direction.

23. The method according to claim 22, wherein the evaluating comprises identifying a region of abnormal depolarization wave conduction.

24. The method according to claim 22, wherein the evaluating comprises identifying pre-ischemic or ischemic region of the tissue.

25. The method according to claim 22, wherein the evaluating comprises identifying an ischemic region of the tissue.

26. The method according to claim 25, wherein the region of abnormal depolarization wave conduction is characterized by a nonlinear wave propagation.

27. The method according to claim 26, wherein the nonlinear wave propagation is a curvilinear propagation.

28. The method according to claim 23, wherein the method further comprises applying a stimulus to the tissue in a manner sufficient to compensate for the region of abnormal depolarization wave conduction.

29. The method according to claim 28, wherein the method comprises employing a cardiac wavefront controller to apply the stimulus.

30. The method according to claim 29, wherein the cardiac wavefront controller applies an electrical stimulus to the tissue from two or more different effectors associated with the first, second, third, or fourth satellite in a manner sufficient to compensate for the region of abnormal depolarization wave conduction.

31. The method according to claim 30, wherein the cardiac wavefront controller sequentially applies the electrical stimulus to the tissue from the two or more different effectors.

32. A method of stimulating cardiac tissue, the method comprising:
locating a first satellite coupled to a central controller relative to the tissue, the first satellite having a first satellite circuit and at least two first satellite electrodes, the first satellite circuit adapted to individually reconfigurably couple and decouple each of the at least two first satellite electrodes as directed by the central controller;
locating a second satellite coupled to the central controller relative to the tissue, the second satellite having a second satellite circuit and at least two second satellite electrodes, the second satellite circuit adapted to individually reconfigurably couple and decouple each of the at least two second satellite electrodes as directed by the central controller;
determining a time interval between a first satellite's reporting of a depolarization wave in the tissue and a second satellite's reporting of a depolarization wave in the tissue, wherein the first satellite and the second satellite are formed on a lead, and wherein the second satellite is located a fixed distance away from the first satellite;
calculating a conduction velocity using the time interval and the fixed distance between the first satellite and the second satellite;
identifying a region of abnormal depolarization wavefront conduction in the tissue using at least the conduction velocity; and
applying a stimulus to the tissue in a manner sufficient to compensate for the region of abnormal depolarization wave conduction.

33. The method according to claim 32, wherein the method comprises employing a cardiac wavefront controller to apply the stimulus.

34. The method according to claim 33, wherein the cardiac wavefront controller applies an electrical stimulus to the tissue from two or more different effectors associated with the first and second satellites in a manner sufficient to compensate for the region of abnormal depolarization wave conduction.

35. The method according to claim 34, wherein the cardiac wavefront controller sequentially applies the electrical stimulus to the tissue from the two or more different effectors.

36. A system for determining conduction velocity of a depolarization wave in a tissue, the system comprising:
(a) locating a first satellite coupled to a central controller relative to the tissue, the first satellite having a first satellite circuit and at least two first satellite electrodes, the first satellite circuit adapted to individually reconfigurably couple and decouple each of the at least two first satellite electrodes as directed by the central controller;
(b) locating a second satellite coupled to the central controller relative to the tissue, the second satellite having a second satellite circuit and at least two second satellite electrodes, the second satellite circuit adapted to individually reconfigurably couple and decouple each of the at least two second satellite electrodes as directed by the central controller;
(c) the first satellite and the second satellite positioned a fixed distance away from the first satellite, wherein each of the first and second satellite is configured to report a depolarization wave in the tissue; and
(d) a signal processing element configured to:
(i) determine a time interval between the first satellite's reporting of a depolarization wave in the tissue and the second satellite's reporting of the depolarization wave in the tissue; and
(ii) calculate a conduction velocity of the depolarization wave in the tissue using the time interval and the fixed distance between the first satellite and the second satellite.

37. The system according to claim 36, wherein the first and second satellites are coupled to at least one conductive element within the lead.

38. The system according to claim 37, wherein the at least one conductive element is coupled to the central controller.

39. The system according to claim 38, wherein the signal processing element is formed at the central controller.

40. The system according to claim 39, wherein the central controller is formed in an implantable control device.

41. The system according to claim 40, wherein the system further comprises a third and fourth satellites formed on a second lead.

42. The system according to claim 36, wherein the system further comprises a cardiac wavefront controller.

43. A non-transitory computer readable storage medium having a processing program stored thereon, wherein the processing program, when executed by a processor, is configured to perform a method comprising:

directing a first satellite having at least two first satellite electrodes to individually reconfigurably couple and decouple each of at least two first satellite electrodes as directed by a central controller;

directing a second satellite having at least two second satellite electrodes to individually reconfigurably couple and decouple each of at least two second satellite electrodes as directed by the central controller;

determining a time interval between a first satellite's reporting of a depolarization wave in a tissue and a second satellite's reporting of a depolarization wave in the tissue, wherein the first satellite and the second satellite are formed on a lead, and wherein the second satellite is located a fixed distance away from the first satellite; and calculating a conduction velocity using the time interval and the fixed distance between the first satellite and the second satellite.

* * * * *